US006646264B1

(12) United States Patent
Modiano et al.

(10) Patent No.: US 6,646,264 B1
(45) Date of Patent: Nov. 11, 2003

(54) METHODS AND DEVICES FOR ANALYZING AGRICULTURAL PRODUCTS

(75) Inventors: Steven H. Modiano, Ballwin, MO (US); Kevin L. Deppermann, St. Charles Mission, MO (US)

(73) Assignee: Monsanto Technology LLC, St. Louis, MO (US)

( * ) Notice: Subject to any disclaimer, the term of this patent is extended or adjusted under 35 U.S.C. 154(b) by 421 days.

(21) Appl. No.: 09/698,214

(22) Filed: Oct. 30, 2000

(51) Int. Cl.[7] ............................................. G01N 21/35
(52) U.S. Cl. ........................ 250/339.07; 250/339.12; 356/305; 356/326; 356/328
(58) Field of Search .................. 356/326, 328, 356/305; 250/339.07, 339.12, 910

(56) References Cited

U.S. PATENT DOCUMENTS

| 3,861,788 | A | | 1/1975 | Webster ................... 350/315 |
| 4,037,970 | A | | 7/1977 | Webster et al. ........... 356/188 |
| 4,040,747 | A | | 8/1977 | Webster ................... 356/188 |
| 4,260,262 | A | | 4/1981 | Webster ................... 356/418 |
| 4,734,584 | A | | 3/1988 | Rosenthal ................. 250/343 |
| 4,752,689 | A | | 6/1988 | Satake ..................... 250/339 |
| 5,132,538 | A | | 7/1992 | Norris ..................... 250/339 |
| 5,475,221 | A | | 12/1995 | Wang .................... 250/339.07 |
| 5,533,145 | A | * | 7/1996 | Shofner et al. ............ 356/328 |
| 5,668,374 | A | | 9/1997 | DiFoggio et al. ........ 250/339.12 |
| 5,751,421 | A | | 5/1998 | Wright et al. ............. 356/328 |
| 5,918,977 | A | | 7/1999 | Borggaard et al. ........ 366/140 |
| 5,991,025 | A | | 11/1999 | Wright et al. ............. 356/328 |
| 6,100,526 | A | | 8/2000 | Mayes ................... 250/339.11 |
| 2001/0014750 | A1 | | 8/2001 | Ulrich et al. .............. 554/14 |

FOREIGN PATENT DOCUMENTS

| DE | 0 539 537 B2 | 12/2000 |
| EP | 0 636 310 A1 | 2/1995 |
| EP | 0 511 184 B1 | 6/1998 |
| WO | WO 96/24830 | 8/1996 |
| WO | WO 98/44140 | 10/1998 |
| WO | WO 99/40419 | 8/1999 |
| WO | WO 99/58959 | 11/1999 |
| WO | WO 00/71993 A1 | 11/2000 |
| WO | WO 01/89288 A1 | 11/2001 |

OTHER PUBLICATIONS

International Search Report, PCT/US01/51007, dated Jun. 20, 2002.

"Seed Meister Luminar 3076", Brimrose Corporation of America, Baltimore, MD, http://www.brimrose.com/seed_meister.html; date unknown.

P.A. Hailey—Pfizer Central Research, "The Role of NIR Spectroscopy in the Measurement of Pharmaceutical Manufacture", http://wwwbrimrose.com/hailey.html; date unknown.

Dr. Jolanta Soos, "Industrial Process Monitoring Requires Rugged AOTF Tools", *Laser Focus World*, Aug. 1994.

"Rapid identification of organic contaminants in retreated waste water using AOTF near–IR spectrometry", *ISA 1995 Meeting Proceedings*, pp. 87–95, 1995.

Archibald et al., "Development of Short–Wavelength Near–Infrared Spectral Imaging for Grain Color Classification," SPIE vol. 3543, 1998, pp. 189–198.

(List continued on next page.)

*Primary Examiner*—F. L. Evans
(74) *Attorney, Agent, or Firm*—Jenkens & Gilchrist, P.C.

(57) ABSTRACT

The present invention relates to a device and method for analyzing agricultural products. More particularly, the present invention relates to a device and method for real time, non-destructive analysis of the physical and chemical characteristics of one or more seeds.

209 Claims, 25 Drawing Sheets

OTHER PUBLICATIONS

Daun et al., "Comparison of Three Whole Seed Near–Infrared Analyzers for Measuring Quality Components of Canola Seed", vol. 71, No. 10, 1994, pp. 1063–1068.

Delwiche, "Single Wheat Kernel Analysis by Near–Infrared Transmittance: Protein Content," Analytical Techniques and Instrumentation, vol. 72, No. 1, 1995, pp. 11–16.

Dowell, "Automated Color Classification of Single Wheat Kernels Using Visible and Near–Infrared Reflectance," Cereal Chemistry, vol. 75(1), 1998, pp. 142–144.

Dowell et al., "Automated Single Wheat Kernel Quality Measurement Using Near–Infrared Reflectance," ASAE Annual International Meeting, 1997, paper No. 973022.

Massie and Norris, "Spectral Reflectance and Transmittance Properties of Grain in the Visible and near Infrared", Transactions of the ASAE, Winter Meeting of the American Society of Agricultural Engineers, 1965, pp. 598–600.

Orman and Schumann, "Comparison of Near–Infrared Spectroscopy Calibration Methods for the Prediction of Protein, Oil, and Starch in Maize Grain," J. Agric. Food Chem. vol. 39, 1991, pp. 883–886.

Robutti, "Maize Kernel Hardness Estimation in Breeding by Near–Infrared Transmission Analysis," Analytical Techniques and Instrumentation vol. 72, No. 6, 1995, pp. 632–636.

* cited by examiner

Averaged Reflectance Spectra for 96 Bulk Corn Samples Used for Calibration Model Development Typical Reflectance Spectra for the Bulk Corn Samples Used for Calibration Model Development

Figure 18
Summary of Partial Least Squares (PLS)
Type 2 Model Performance, Full Cross Validation

| Component | $R^2$ | SEP | Slope | Bias |
|---|---|---|---|---|
| Oil | 0.962 | 0.48 | 0.93 | 0.0069 |
| Protein | 0.936 | 0.87 | 0.88 | -0.018 |
| Starch | 0.954 | 0.75 | 0.91 | 0.0016 |
| Moisture | 0.496 | 0.78 | 0.32 | -0.0033 |

6 Principle Components used in Model

Typical Reflectance Spectra for the Single Kernel Corn Samples Used for Calibration Model Development Total Explained Validation Variance vs. PC #, Single Kernel Corn

METHODS AND DEVICES FOR ANALYZING AGRICULTURAL PRODUCTS

FIELD OF THE INVENTION

The present invention relates to a device and method for analyzing agricultural products. More particularly, the present invention relates to a device and method for real time, non-destructive analysis of the physical and chemical characteristics of one or more seeds.

BACKGROUND OF THE INVENTION

Breeding for compositionally enhanced agricultural products can require the analysis of a large number of seed samples from plants to identify those plants with the desired compositional and agronomic properties for use or advancement to the next generation. Analysis of bulk seed batches for certain traits, such as high oil or high protein, on a single plant or ear, in conjunction with an appropriate breeding methodology such as recurrent selection, often allow for the selection of and introduction of such traits into a commercial population. Although the analysis of these seed batches can be performed by various techniques, typically methods that are rapid, low cost, and non-destructive are used.

During the past decade, near infrared (NIR) spectroscopy has become a standard method for screening seed samples whenever the sample of interest has been amenable to this technique. Samples studied include wheat, maize, soybean, canola, rice, alfalfa, oat, and others (see, for example, Massie and Norris, "Spectral Reflectance and Transmittance Properties of Grain in the Visible and Near Infrared", Transactions of the ASAE, Winter Meeting of the American society of Agricultural Engineers, 1965, pp. 598–600, which is herein incorporated by reference in its entirety). NIR spectroscopy uses near infrared light, which is typically in the range of 770 to 2,500 nanometers, to access overtones and combinations of the fundamental vibrational frequencies of the organic functional groups of O—H, C—H, and N—H. Devices for measuring such light are known in the art. (See, for example Hyvarinen et al., "Direct Sight Imaging Spectrograph: A Unique Add-on Component Brings Spectral Imaging to Industrial Applications", SPIE Vol. 3,302, 1998, "Handbook of Near-Infrared Analysis", Eds. Burns and Ciurczak, Marcel Dekker, Inc., 1992, both of which are herein incorporated by reference in their entirety).

Typically, the NIR spectra associated with a batch of seeds is determined (often, for example, a cuvette capable of holding 100 grams of seed is used). This determination can be combined with conventional chemical analysis of samples in order to provide additional data and to build a chemometric calibration model. Chemometric calibration models are often developed for traits that include, but are not limited to: oil, starch, water, fiber, protein, extractable starch, chlorophyll, glucosinolates, and fatty acid (see, for example, Archibald et al. "Development of Short-Wavelength Near-Infrared spectral Imaging for Grain Color Classification," SPIE Vol. 3,543, 1998, pp. 189–198, Delwiche, "Single Wheat Kernel Analysis by Near-Infrared Transmittance: Protein Content," Analytical Techniques and Instrumentation, Vol. 72, 1995, pp. 11–16, Dowell, "Automated Color Classification of single Wheat Kernels Using Visible and Near-Infrared Reflectance," Vol. 75(1), 1998, pp. 142–144, Orman and Schumann, "Comparison of Near-Infrared Spectroscopy Calibration Methods for the Prediction of Protein, Oil, and Starch in Maize Grain," Vol. 39, 1991, pp.883–886, Robutti, "Maize Kernel Hardness Estimation in Breeding by Near-Infrared Transmission Analysis," Vol. 72(6), 1995, pp.632–636, U.S. Pat. No. 5,991,025, U.S. Pat. No. 5,751,421, Daun et al., "Comparison of Three whole Seed Near-Infrared Analyzers for Measuring Quality Components of Canola Seed", Vol. 71, no. 10, 1994, pp. 1,063–1,068, "Corn: Chemistry and Technology", Eds. Watson and Ramstad, American Association of Cereal Chemists, Inc., (1987), all of which are herein incorporated by reference in their entirety). The development of a chemometric model can then be used to predict the chemical characteristics of untested samples with NIR spectroscopy, without requiring additional conventional chemical analysis.

NIR analysis of bulk samples, either crushed or whole, has been reported (see, for example, Orman and Schumann, "Comparison of Near-Infrared Spectroscopy Calibration Methods for the Prediction of Protein, Oil, and Starch in Maize Grain," Vol. 39, 1991, pp.883–886, Robutti, "Maize Kernel Hardness Estimation in Breeding by Near-Infrared Transmission Analysis," Vol. 72(6), 1995, pp.632–636, U.S. Pat. No. 5,991,025, U.S. Pat. No. 5,751,421, Daun et al., "Comparison of Three whole Seed Near-Infrared Analyzers for Measuring Quality Components of Canola Seed", Vol. 71, no. 10, 1994, pp.1,063–1,068, all of which are herein incorporated by reference in their entirety). Conventional commercial NIR spectrometers for bulk grain analysis have several disadvantages. Conventional spectrometers were designed for use in a laboratory environment, which is typically distant from the breeding fields, under controlled conditions of temperature, humidity and vibration. In addition, the spectrometers necessitate excessive sample handling. The samples must be harvested, sent to the breeding facility, threshed, bagged, labeled, and sent to the NIR lab for analysis. At the NIR lab the samples must be logged in, removed from the sample bags, poured into the sample cuvette, scanned with the NIR spectrometer, returned to the original sample bag, and sent back to the breeding facility. The resulting NIR data must be assembled into a final report, reviewed for any anomalies, and sent back to the breeder, who then locates and sorts the samples based upon the NIR analytical results. The excessive sample handling adds both time and cost to the analysis.

Current NIR based approaches are not only cumbersome and expensive, they are slow. Data processing time can be crucial because selection of appropriate seeds should be carried out prior to the planting time of the next generation. Delays in providing the breeder with the analytical results or the return of the samples can result in the loss of an entire breeding cycle.

Further, the speed of acquisition and analysis of the current technology cannot keep up with the speed at which the processing devices can operate. For example, single ear shellers can process up to 15 ears of corn per minute. Current NIR commercial spectrometers operate at a rate of about one sample every one to two minutes. The spectrometer rate of processing is typically the limiting step in the analytical process.

Conventional spectrometers gather information from a sub-set of the total sample. Commercial spectrometers collect light at a single point or several tens of points with small active areas, which results in only a small portion of the sample actually being interrogated by the technique. In bulk samples, for example, conventional techniques can lead to spot sampling of portions of only a few seeds out of the hundreds of seeds in the bulk sample. Further, since spot sampling of bulk samples analyzes arbitrary portions of the seed, different tissues of the seeds in the samples can be misrepresented by the analytical data. Since qualities like oil content are often present in different amounts in different tissues, these conventional techniques can fail to accurately assess the desired quality. These limitations apply to spectrometers with conventional optical configurations where a lens system collects light from the sample, as well as those that use fiber optic bundles to collect the light from the sample. In addition, since discrete, unrelated sampling points are used, spatial information associated with the sample is lost. Spatial information (which can be used, for instance, to determine morphology) consists of, for example, size, shape, mechanical damage, insect infestation, and fungal damage. Since conventional spectrometers do not collect spatial information at all, a correlation of spatial and spectral data is not possible.

Conventional spectrometers also fail to provide an efficient method for single seed analysis, which can greatly accelerate the rate of varietal development. Single seed analysis is necessary to differentiate and select seed present within a heterogeneous population of seeds. Heterogeneous populations of seed are often encountered in breeding populations. Single seed analysis can reduce the number of generations required for the production of a plant with the desired trait. Single seed selection also reduces the number of individual plants required. In corn, for example, the ability to identify the individual seeds with the desired trait at the single seed level rather than at the whole ear level can reduce the nursery requirement by 100 fold. This makes it possible to conduct a far greater number of breeding projects with the same resources.

NIR analysis of single seeds has also been reported (see Delwiche, "Single Wheat Kernel Analysis by Near-Infrared Transmittance: Protein Content," Analytical Techniques and Instrumentation, Vol. 72, 1995, pp. 11–16, Dowell, "Automated Color Classification of single Wheat Kernels Using Visible and Near-Infrared Reflectance," Vol. 75(1), 1998, pp. 142–144, Dowell et al., "Automated Single Wheat Kernel Quality Measurement Using Near-Infrared Reflectance," ASAE Annual International Meeting, 1997, paper number 973022, all of which are herein incorporated by reference in their entirety). These methods, however, measure light from the entire seed to calculate average intensities, and therefore are not capable of providing information about single seeds beyond whole seed averages.

Other conventional analytical techniques, such as gas chromatography, also often fail to provide an efficient method for single seed analysis. For example, the conventional method for single seed analysis of canola requires manual excision of one half of each seed for fatty acid analysis by gas chromatography, while the other half is planted. Because of the manual sample preparation and the low throughput of this analytical technique, only a small number of samples can be run per hour using this process.

Although single seed analysis is desirable, conventional spectrometers and sampling methods do not allow for efficient processing of single seeds. Conventional techniques require extensive manual input, which limits the rate of development of plants with improved characteristics.

Conventional spectrometric analysis techniques do not allow for the localization of chemical component levels within different tissues of seeds. Conventional approaches, such as manual dissection of the seed followed by chemical analysis by traditional analytical techniques, are not only laborious and destructive, they also results in poor resolution of the components and poor quantitation, since the sample size resulting from dissection of individual seeds is below the sample size at which most traditional techniques produce reliable results.

Certain conventional imaging systems image the entire sample simultaneously using a tunable filter to limit light from a sample to a single wavelength (see Archibald et al., "Development of Short-Wavelength Near-Infrared spectral Imaging for Grain Color Classification," SPIE Vol. 3,543, 1998, pp. 189–198, which is herein incorporated by reference in its entirety). This method has limited usefulness because even illumination of the sample is difficult to achieve. Uneven illumination of the sample causes areas of low image quality, which limits the accuracy of any information gained from the system. Further, the use of tunable filters is time consuming, which significantly slows the analytical process.

Needed in the art are devices and methods for rapid analysis of bulk and single seeds that can efficiently and non-destructively analyze the morphological or chemical characteristics of individual seeds, and that can be integrated into an agricultural processing machine. The present invention provides such devices and methods.

SUMMARY OF THE INVENTION

The present invention provides devices and methods for real time, non-destructive analysis of the physical and chemical characteristics of one or more seeds. Analysis can be carried out by directing light at a sample, which forms transmitted or reflected light. Transmitted or reflected light from the sample can then be dispersed into different wavelengths, which are detected with a datapoint array. Signals produced by the datapoint array can be used to determine the value of any of many chemical and morphological traits.

The present invention includes and provides a method for determining whether a seed exhibits a trait comprising: (A) providing the seed in a sampling device; (B) directing light from a light source to the seed, thereby forming reflected light; (C) passing the reflected light through a spectrograph to form dispersed light; (D) receiving the dispersed light in a light measuring device comprising an array of multiple datapoints; (E) outputting a signal for each of the multiple datapoints with the light measuring device; and, (F) determining whether the seed exhibits the trait based on the signals.

The present invention includes and provides a method for determining whether a seed exhibits a trait comprising: (A) providing the seed in a sampling device; (B) directing light from a light source to the seed, thereby forming transmitted light; (C) passing the transmitted light through a spectrograph to form dispersed light; (D) receiving the dispersed light in a light measuring device comprising an array of multiple datapoints; (E) outputting a signal for each of the multiple datapoints with the light measuring device; and, (F) determining whether the seed exhibits the trait based on the signals.

The present invention includes and provides a method for determining whether a plant tissue exhibits a trait comprising: (A) providing the plant tissue in a sampling device; (B) directing light from a light source to the plant tissue, thereby forming transmitted or reflected light; (C) passing the transmitted or reflected light through a spectrograph, thereby forming dispersed light; (D) receiving the dispersed light in a light measuring device comprising an array of multiple datapoints; (E) outputting a signal for each of the multiple datapoints with the light measuring device; and, (F) determining whether the plant tissue exhibits the trait based on the signals.

The present invention includes and provides a method for determining whether a seed exhibits a trait comprising: (A) providing the seed in a sampling device; (B) directing light from a light source to the seed, thereby forming reflected light; (C) dispersing the reflected light to form dispersed light; (D) receiving the dispersed light in a light measuring device comprising an array of multiple datapoints; (E) outputting a signal for each of the multiple datapoints with the light measuring device; and, (F) determining whether the seed exhibits the trait based on the signals.

The present invention includes and provides a method for determining whether a seed exhibits a trait comprising: (A) providing the seed in a sampling device; (B) directing light from a light source to the seed, thereby forming transmitted light; (C) dispersing the transmitted light to form dispersed light; (D) receiving the dispersed light in a light measuring device comprising an array of multiple datapoints; (E) outputting a signal for each of the multiple datapoints with the light measuring device; and, (F) determining whether the seed exhibits the trait based on the signals.

The present invention includes and provides a method for determining whether a plant tissue exhibits a trait comprising: (A) providing the plant tissue in a sampling device; (B) directing light from a light source to the plant tissue, thereby forming transmitted or reflected light; (C) dispersing the transmitted or reflected light to form dispersed light; (D) receiving the dispersed light in a light measuring device comprising an array of multiple datapoints; (E) outputting a signal for each of the multiple datapoints with the device; and, (F) determining whether plant tissue seed exhibits the trait based on the signals.

The present invention includes and provides a method for determining whether a batch of seeds contains seeds which exhibit a trait comprising: (A) providing the batch of seeds in a sampling device; (B) directing light from a light source to the batch of seed, thereby forming reflected light; (C) passing the reflected light through a spectrograph to form dispersed light; (D) receiving the dispersed light in a light measuring device comprising an array of multiple datapoints; (E) outputting a signal for each of the multiple datapoints with the light measuring device; and, (F) determining whether members of the batch of seed exhibits the trait based on the signals, wherein the determining comprises associating the members with corresponding datapoints.

The present invention includes and provides a method for determining whether a batch of seeds contains seeds which exhibit a trait comprising: (A) providing the batch of seeds in a sampling device; (B) directing light from a light source to the batch of seed, thereby forming transmitted light; (C) passing the transmitted light through a spectrograph to form dispersed light; (D) receiving the dispersed light in a light measuring device comprising an array of multiple datapoints; (E) outputting a signal for each of the multiple datapoints with the light measuring device; and, (F) determining whether members of the batch of seed exhibits the trait based on the signals, wherein the determining comprises associating the members with corresponding datapoints.

The present invention includes and provides a method for determining whether a batch of seeds contains seeds which exhibit a trait comprising: (A) providing the batch of seeds in a sampling device; (B) directing light from a light source to the batch of seed, thereby forming reflected light and transmitted light; (C) passing the reflected light or the transmitted light through a spectrograph to form dispersed light; (D) receiving the dispersed light in a light measuring device comprising an array of multiple datapoints; (E) outputting a signal for each of the multiple datapoints with the light measuring device; and, (F) determining whether members of the batch of seed exhibits the trait based on the signals, wherein the determining comprises associating the members with corresponding datapoints.

The present invention includes and provides a method for determining whether a seed exhibits multiple traits comprising: (A) providing the seed in a sampling device; (B) directing light from a light source to the seed, thereby forming reflected light; (C) passing the reflected light through a spectrograph to form dispersed light; (D) receiving the dispersed light in a light measuring device comprising an array of multiple datapoints; (E) outputting a signal for each of the multiple datapoints with the light measuring device; and, (F) determining whether the seed exhibits each of the traits based on the signals.

The present invention includes and provides a method for determining whether a seed exhibits multiple traits comprising: (A) providing the seed in a sampling device; (B) directing light from a light source to the seed, thereby forming transmitted light; (C) passing the transmitted light through a spectrograph to form dispersed light; (D) receiving the dispersed light in a light measuring device comprising an array of multiple datapoints; (E) outputting a signal for each of the multiple datapoints with the light measuring device; and, (F) determining whether the seed exhibits each of the traits based on the signals.

The present invention includes and provides a method for determining whether a seed exhibits multiple traits comprising: (A) providing the seed in a sampling device; (B) directing light from a light source to the seed, thereby forming reflected light and transmitted light; (C) passing the reflected light or the transmitted light through a spectrograph to form dispersed light; (D) receiving the dispersed light in a light measuring device comprising an array of multiple datapoints; (E) outputting a signal for each of the multiple datapoints with the light measuring device; and, (F) determining whether the seed exhibits each of the traits based on the signals.

The present invention includes and provides a method for selecting a seed having a trait, comprising: (A) providing the seed in a sampling device; (B) directing light from a light source to the seed, thereby forming transmitted or reflected light; (C) passing the transmitted or reflected light through a spectrograph; (D) receiving the transmitted light or reflected light in a light measuring device comprising an array of multiple datapoints; (E) outputting a signal for each of the multiple datapoints with the device; (F) determining whether the seed exhibits the trait based on the signals; and (G) selecting the seed having the trait based on the signals.

The present invention includes and provides a method of introgressing a trait into a plant comprising: (A) providing the seed in a sampling device; (B) directing light from a light source to a seed and generating transmitted or reflected light; (C) passing the transmitted or reflected light through a spectrograph; (D) receiving the transmitted light or reflected light in a light measuring device comprising an array of multiple datapoints; (E) outputting a signal for each of the multiple datapoints with the device; (F) determining whether the seed exhibits the trait based on the signals; (G) selecting the seed having the trait based on the signals; (H) growing a fertile plant from the seed; and, (I) utilizing the fertile plant as either a female parent or a male parent in a cross with a second plant.

The present invention includes and provides a method for determining whether a seed exhibits a trait comprising: (A) providing the seed in a sampling device; (B) directing light from a light source to the seed, thereby forming reflected light; (C) passing the reflected light through a spectrograph to form dispersed light, wherein a first line of the reflected light from the sample passes through the spectrograph; (D) receiving the dispersed light in a light measuring device comprising an array of multiple datapoints; (E) outputting a signal for each of the multiple datapoints with the light measuring device; (F) repeating steps (A) through (E) for subsequent lines of the reflected light; and, (G) determining whether the seed exhibits the trait based on the signals.

The present invention includes and provides a method for determining whether a seed exhibits a trait comprising: (A) providing the seed in a sampling device; (B) directing light from a light source to the seed, thereby forming reflected light; (C) passing the reflected light through a spectrograph to form dispersed light, wherein one or more subsequent lines of the reflected light from the sample passes through the spectrograph; (D) receiving the dispersed light in a light measuring device comprising an array of multiple datapoints; (E) outputting a signal for each of the multiple datapoints with the light measuring device; (F) repeating steps (A) through (E) for subsequent lines of the reflected light; and, (G) determining whether the seed exhibits the trait based on the signals.

The present invention includes and provides a method for determining whether a seed exhibits a trait comprising: (A) providing the seed in a sampling device; (B) directing light from a light source to the seed, thereby forming transmitted light; (C) passing the reflected light through a spectrograph to form dispersed light, wherein a first line of the reflected light from the sample passes through the spectrograph; (D) receiving the dispersed light in a light measuring device comprising an array of multiple datapoints; (E) outputting a signal for each of the multiple datapoints with the light measuring device; (F) repeating steps (A) through (E) for subsequent lines of the reflected light; and, (G) determining whether the seed exhibits the trait based on the signals.

The present invention includes and provides a method for determining whether a seed exhibits a trait comprising: (A) providing the seed in a sampling device; (B) directing light from a light source to the seed, thereby forming transmitted light; (C) passing the reflected light through a spectrograph to form dispersed light, wherein one or more subsequent lines of the reflected light from the sample passes through the spectrograph; (D) receiving the dispersed light in a light measuring device comprising an array of multiple datapoints; (E) outputting a signal for each of the multiple datapoints with the light measuring device; (F) repeating steps (A) through (E) for subsequent lines of the reflected light; and, (G) determining whether the seed exhibits the trait based on the signals.

The present invention includes and provides a method for determining whether a seed exhibits a trait comprising: (A) providing the seed in a sampling device; (B) directing light from a light source to the seed, thereby forming reflected light and transmitted light; (C) passing the reflected light or the transmitted light through a spectrograph to form dispersed light, wherein a first line of the reflected light from the sample passes through the spectrograph; (D) receiving the dispersed light in a light measuring device comprising an array of multiple datapoints; (E) outputting a signal for each of the multiple datapoints with the light measuring device; (F) repeating steps (A) through (E) for subsequent lines of the reflected light; and, (G) determining whether the seed exhibits the trait based on the signals.

The present invention includes and provides a method for determining whether a seed exhibits a trait comprising: (A) providing the seed in a sampling device; (B) directing light from a light source to the seed, thereby forming reflected light and transmitted light; (C) passing the reflected light or the transmitted light through a spectrograph to form dispersed light, wherein one or more subsequent lines of the reflected light from the sample passes through the spectrograph; (D) receiving the dispersed light in a light measuring device comprising an array of multiple datapoints; (E) outputting a signal for each of the multiple datapoints with the light measuring device; (F) repeating steps (A) through (E) for subsequent lines of the reflected light; and, (G) determining whether the seed exhibits the trait based on the signals.

The present invention includes and provides a method for simultaneously determining whether a batch of seeds contains seeds which exhibit a trait comprising: (A) providing the batch of seeds in a sampling device; (B) directing light from a light source to the batch of seed, thereby forming reflected light; (C) passing the reflected light through a spectrograph to form dispersed light; (D) receiving the dispersed light in a light measuring device comprising an array of multiple datapoints; (E) outputting a signal for each of the multiple datapoints with the light measuring device; and, (F) determining whether members of the batch of seed exhibits the trait based on the signals, wherein the determining comprises associating the members with corresponding datapoints.

The present invention includes and provides a method for simultaneously determining whether a batch of seeds contains seeds which exhibit a trait comprising: (A) providing the batch of seeds in a sampling device; (B) directing light from a light source to the batch of seed, thereby forming transmitted light; (C) passing the transmitted light through a spectrograph to form dispersed light; (D) receiving the dispersed light in a light measuring device comprising an array of multiple datapoints; (E) outputting a signal for each of the multiple datapoints with the light measuring device; and, (F) determining whether members of the batch of seed exhibits the trait based on the signals, wherein the determining comprises associating the members with corresponding datapoints.

The present invention includes and provides a method for simultaneously determining whether a batch of seeds contains seeds which exhibit a trait comprising: (A) providing the batch of seeds in a sampling device; (B) directing light from a light source to the batch of seed, thereby forming reflected light and transmitted light; (C) passing the reflected light or the transmitted light through a spectrograph to form dispersed light; (D) receiving the dispersed light in a light measuring device comprising an array of multiple datapoints; (E) outputting a signal for each of the multiple datapoints with the light measuring device; and, (F) determining whether members of the batch of seed exhibits the trait based on the signals, wherein the determining comprises associating the members with corresponding datapoints.

The present invention includes and provides a device for measuring properties of agricultural products, comprising: a processing device for producing a sample; a sampling device for providing a sample, wherein the sampling device is disposed to receive the sample from the processing device; and, an optical spectroscopic imaging system, wherein the system is disposed to analyze the sample in the sampling device.

The present invention includes and provides a device for measuring properties of agricultural products, comprising: a sampling device for providing a sample; an optical spectroscopic imaging system, wherein the system is disposed to analyze the sample in the sampling device; and, a sorting device for sorting the sample into two or more different groups, wherein the sorting device is disposed to receive the sample from the sampling device.

The present invention includes and provides a device for measuring properties of agricultural products, comprising: a processing device for producing a sample; a sampling device for providing a sample, wherein the sampling device is disposed to receive the sample from the processing device; an optical spectroscopic imaging system, wherein the system is disposed to analyze the sample in the sampling device; and, a sorting device for sorting the sample into two or more different groups, wherein the sorting device is disposed to receive the sample from the sampling device.

DESCRIPTION OF THE FIGURES

FIG. 18 is a summary of partial least squares (PLS) type 2 model performance, full cross validation for oil, protein, starch, moisture.

DETAILED DESCRIPTION OF THE INVENTION

Analytical Methods

Figure 1:
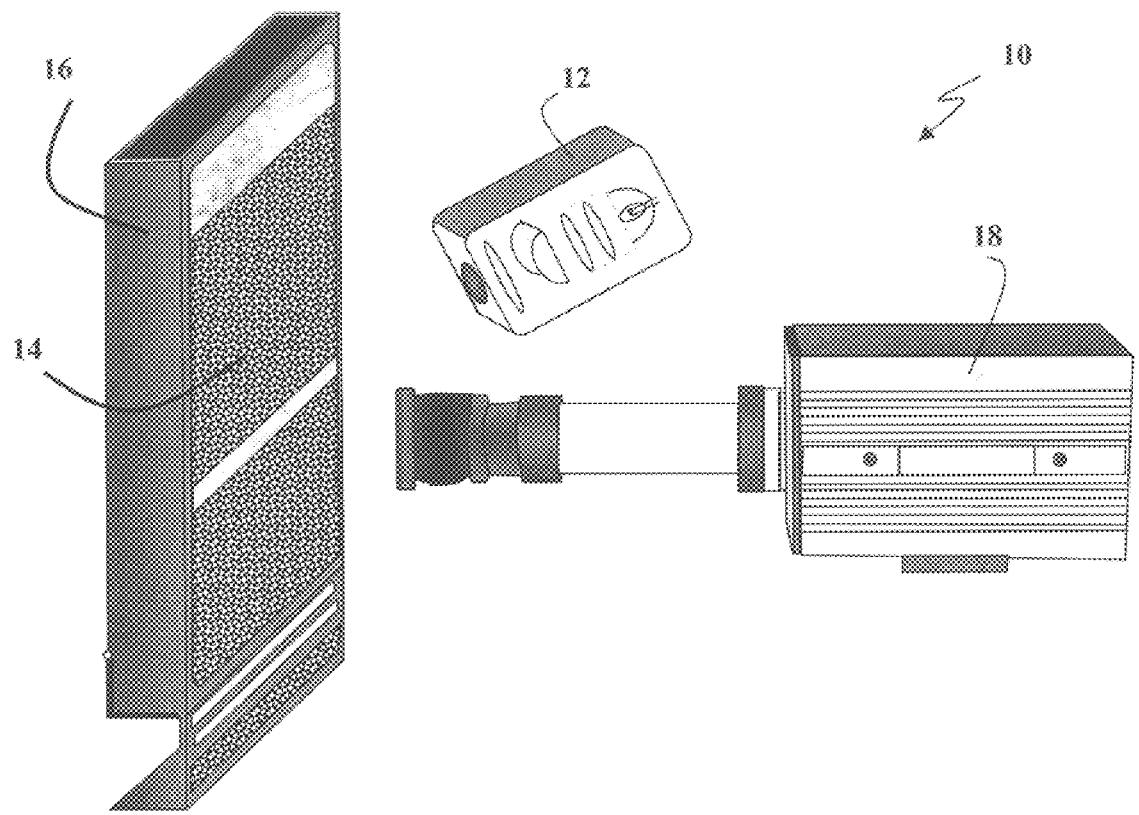
FIG. 1 is a schematic diagram of one embodiment of a light source, a sampling device, and a light measuring device.

The present invention provides analytical methods for analyzing seeds having a desired trait. In an aspect of the invention, the analytical methods allow discrete portions or attributes of a single seed to be analyzed. Moreover, in another aspect of the present invention, the analytical methods allow individual seeds to be analyzed that are present in a batch or a bulk sample such that a distribution of a characteristic can be determined.

In one embodiment, the present invention provides a method for determining whether a seed exhibits a trait comprising: (A) providing the seed in a sampling device; (B) directing light from a light source to the seed, thereby forming reflected light; (C) passing the reflected light through a spectrograph to form dispersed light; (D) receiving the dispersed light in a light measuring device comprising an array of multiple datapoints; (E) outputting a signal for each of the multiple datapoints with the light measuring device; and, (F) determining whether the seed exhibits the trait based on the signals.

In another embodiment, the present invention provides a method for determining whether a seed exhibits a trait comprising: (A) providing the seed in a sampling device; (B) directing light from a light source to the seed, thereby forming transmitted light; (C) passing the transmitted light through a spectrograph to form dispersed light; (D) receiving the dispersed light in a light measuring device comprising an array of multiple datapoints; (E) outputting a signal for each of the multiple datapoints with the light measuring device; and, (F) determining whether the seed exhibits the trait based on the signals.

The methods of the present invention can be used to detect any trait that can be measured by NIR. In one preferred embodiment, the trait is a biochemical trait. As used herein, a biochemical trait is any trait that affects the chemical composition of the agricultural sample. In a preferred embodiment the biochemical trait is selected from the group consisting of oil content, protein content, carbohydrate content, starch content, fiber content and water content. As used herein content refers to the amount of a component, e.g 5 milligrams (mg) per seed of protein or 5 mg protein per 10 grams of dry weight of tissue. In another preferred embodiment the biochemical trait is selected from the group consisting of oil composition, protein composition, carbohydrate composition, and fiber composition. As used herein, composition refers to biochemical constituents of an agricultural sample, for example, the ratio of high molecule weight proteins to low molecular weight proteins or the ratio of saturated oils to non-saturated oils.

For example, in one embodiment, the methods of the present invention are used to differentiate starch samples with desirable phenotypes. Starch from normal dent or flint corn is composed of about 73% amylopectin (the starch fraction with branched molecules) and 27% amylose (the fraction with linear molecules). Waxy corn (having the wx gene) was first found in China, but waxy mutations have also been found in American dent strains. Starch from this mutant is 100% amylopectin. The endosperm mutant amylose-extender (ae) increases the amylose fraction of starch to 50% and above. The kernel of this corn is characterized by a tarnished, translucent, and partially full appearance. Several other mutant genes, either alone or in combination, affect starch composition by changing the amylose-amylopectin ratio. The characteristic firm opaque starch gel produced by common corn is attributed to the amylose fraction. Properties of the waxy maize starch are the result of the amylopectin sols produced having a characteristic soft translucent paste form. These differences in the native starch gel characteristics carry on through the starch modification processes and are desirable in certain applications. The methods of the present invention can readily discern the different mutant types and can be used as a high throughput, non-destructive screening technique for them.

In another embodiment, for example, the methods of the present invention are used to identify samples having desired endosperm traits. For example, several endosperm mutants that alter the balance of amino acids have been identified. It has been shown that the mutant lines opaque-2 ($o_2$), floury-2 ($fl_2$), and opaque-7 ($o_7$) have reduced zeins (the protein in corn that lacks essential amino acids such as lysine and tryptophan) in the endosperm and increased lysine. Kernels with the opaque-2 gene are characterized by a soft, chalky, non-transparent appearance, with very little hard vitreous endosperm. The methods of the present invention can readily discern the different mutant types and levels of lysine, and therefore can be used as a high through-put, non-destructive screening technique for this trait.

In another embodiment the trait is a morphological trait. As used herein, a morphological trait is any structural trait. Preferred morphological traits are endosperm size, germ size, seed shape, seed size, seed color, seed surface texture, seed weight, seed density, and seed integrity. Seed integrity can be correlated with disease resistance or susceptibility. The presence of holes within a seed coat is often indicative of insect infection.

The correlation of a disease state with a structural change such as holes can be established by challenging samples of the seed to be tested with the organism. As used herein, a "sample" refers to any plant material that is being interrogated by a method of the present invention. A sample can be, for example, a fraction of a seed, a whole seed, more than one seed, and other plant tissues, among others. Controls can include seeds known to be susceptible and resistant. The correlation of the disease to a particular structural change can be established by an appropriate statistical analysis. It is understood that controls need not be run against a particular seed or seed batch once a correlation has been established.

Damage to kernels caused during harvesting, drying, elevating, and moving grain through commercial channels can be determined with the methods of the present invention. Use of modern farming techniques, such as the use of field picker-sheller harvesters, has led to a much higher kernel moisture content in samples than if the samples were allowed to dry on the ear. High moisture content requires the use of artificial drying at temperatures in excess of 80° C., which can lead to stress cracks and kernel breakage. Kernel breakage indicators can include, but are not limited to, the ratio of vitreous to non-vitreous endosperm, kernel density, average kernel weight, pericarp quantity and quality, and kernel size and shape. The methods of the present invention can be used in the identification of breakage and breakage susceptibility, and the in the identification of chemical and physical traits that can minimize these problems.

Any seed can be utilized in a method or device of the present invention. In a preferred embodiment, the seed is selected from the group consisting of alfalfa seed, apple seed, banana seed, barley seed, bean seed, broccoli seed, castorbean seed, citrus seed, clover seed, coconut seed, coffee seed, maize seed, cotton seed, cucumber seed, Douglas fir seed, Eucalyptus seed, Loblolly pine seed, linseed seed, melon seed, oat seed, olive seed, palm seed, pea seed, peanut seed, pepper seed, poplar seed, Radiata pine seed, rapeseed seed, rice seed, rye seed, sorghum seed, Southern pine seed, soybean seed, strawberry seed, sugarbeet seed, sugarcane seed, sunflower seed, sweetgum seed, tea seed, tobacco seed, tomato seed, turf, wheat seed, and *Arabidopsis thaliana* seed. In a more preferred embodiment, the seed is selected from the group consisting of cotton seed, maize seed, soybean seed, rapeseed seed, rice seed and wheat seed. In an even more preferred embodiment, the seed is a maize seed.

Any sampling device can be used if that sampling device can be used with a light source. Sampling devices include, but are not limited to, devices such as containers with at least one surface through which light in the desired wavelength range can pass, as well as sampling devices comprising a generally horizontal surface (with or without side walls) onto which the seed sample can be loaded for analysis. Container sampling devices include, but are not limited to, transparent and translucent containers and opaque containers having at least one transparent or translucent surface. Container sampling devices also include, but are not limited to, sampling devices conventionally used with spectrometers, such as sample cups, sample holders with 2 cm and 2.5 cm path lengths, sample cells, sample holders, and cuvettes. Sampling devices comprising a generally horizontal surface include, but are not limited to, any material onto which seed samples can be placed for analysis, including materials comprising an opaque material for reflectance analysis and materials comprising a translucent or transparent material for transmission analysis. In a preferred embodiment, the sampling device is a transparent cuvette. In another preferred embodiment, the sampling device is any flat black material onto which sample seed can be loaded for reflectance analysis.

Any light source may be used that can provide the broad band illumination for the range of wavelengths used for any particular sample studied and light measuring device used. Particularly preferred light sources are those that can provide light throughout the spectral response range for the light measuring device used. Examples of such light sources include, but are not limited to, halogen, tungsten halogen, long filament halogen, xenon, xenon flash, fluorescent, neon, and mercury. In a preferred embodiment, a tungsten halogen light such as an AS220 lamp from CVI Laser Inc. (CVI Laser Corp., 200 Dorado Pl. SE, PO Box 11308, Albuquerque, N.Mex. 87192) providing light over at least the range of 700 to 1,800 nanometers is used. In another embodiment, a light source producing light over at least the range of 350 to 750 nanometers is used. This light source can be any light source mentioned above, including halogen, tungsten halogen, long filament halogen, xenon, xenon flash, fluorescent, neon, and mercury.

The light source can be directed to a sample to form reflected light and transmitted light. Reflected light is any light that strikes and is emitted from the sample but that does not pass through the sample. To measure reflected light, the light measuring device can be oriented at any angle to the sample relative to the light source. In a preferred embodiment using reflected light, the light measuring device is oriented at an angle of less than 180 degrees relative to the light source. For example, for a flat sampling device positioned horizontally, the light source can be positioned at an angle of 20 degrees from an imaginary line perpendicular to the plane of the sampling device with the intersection of the line and the sample as the vertex, and a light measuring device can be positioned at an angle of 20 degrees from the imaginary line opposite the light source and 40 degrees from the light source with the same vertex. At this orientation, light from the light source will be reflected from the sample to the light measuring device.

Transmitted light is light that passes through the sample and is emitted from the sample on the side opposite the light source. In a preferred embodiment, the light source and the light measuring device are positioned on opposite sides of the sample, and all three are positioned colinearly. For example, a cuvette sampling device having opposing transparent walls between which is disposed bulk sample can be positioned between a light source and a light measuring device. The light from the light source strikes the sample, and some of the light is transmitted through the sample to the other side of the cuvette where it is emitted into the light measuring device.

As used herein, "forming reflected or transmitted light" means directing light from a light source to a sample so that reflected light and/or transmitted light is thereby generated.

Either reflected light or transmitted light or both can be passed through a spectrograph. A spectrograph, as used herein, means a device having optical components that are capable of receiving light of mixed wavelengths, dispersing the mixed wavelength light into its component wavelengths, and emitting the dispersed wavelengths. In a preferred embodiment a spectrograph comprises an entrance slit for receiving light and a prism-grating-prism for dispersing the light. In another embodiment, the spectrograph is a reflective grating spectrograph having either a holographic grating or a fixed groove grating. As used herein, "dispersed" light is light that has been converted from light of mixed wavelengths into light with the component wavelengths separated. "Dispersing" either reflected or transmitted light, as used herein, means separating light of mixed wavelengths into light with the component wavelengths separated. "Passing" either the reflected or transmitted light through a spectrograph, as used herein, means receiving the reflected or transmitted light at an entrance aperture such as a slit such that the light travels through the optics of the spectrograph, is dispersed, and is emitted from an exit aperture. In a preferred embodiment the entrance slit is positioned so as to receive light from the sample, and a light measuring device is affixed to the exit aperture.

The range of wavelengths emitted by the spectrograph can be any range that is broad enough to allow analysis of the sample. In a preferred embodiment, the spectrograph is capable of emitting dispersed light having wavelengths in the range of 500 to 2,000 nanometers, more preferably 700 to 1,800 nanometers, and even more preferably 900 to 1,700 nanometers. In another preferred embodiment the spectrograph is capable of emitting dispersed light having wavelengths in the range of 100 to 1,000 nanometers. The spectrograph preferably has a spectral dispersion of at least 50 nanometers per millimeter (nm/mm), more preferably 100, 125 and 150 nm/mm. The spectrograph preferably has at least 100 nm sprectral resolution, more preferably 50 nm, and even more preferably a 40, 30, and 20 nm spectral resolution. In a preferred embodiment, the spectrograph has a 900 to 1,700 nm spectral range, a spectral dispersion of at least 150 nm/mm and at least a 20 nm spectral resolution The output from the spectrograph may be received in a light measuring device capable of receiving light from the spectrograph at multiple datapoints. As used herein, "datapoint" means a discrete area, such as a focal plane array, at which light can be independently received and measured. These datapoints can be arranged, for example, in multiple dimensions. In a preferred embodiment the multiple datapoints are arranged in a two dimensional array. An array of multiple datapoints can comprise pixels, with each pixel corresponding to a datapoint and being capable of independently receiving light and outputting a signal. In a preferred embodiment, the number of datapoints is greater than 100, more preferably 500, even more preferably 1,000, 5,000, 10,000, 75,000 or 100,000. In a preferred embodiment, the number of pixels is greater than 1,000, more preferably 5,000, even more preferably 10,000, 75,000 or 100,000. Examples of available arrays for measuring multiple datapoints include, but are not limited to, light measuring devices, such as cameras, having arrays for imaging. The light measuring device preferably has less than a 100 micron pitch, and more preferably has less than a 50, 40, 30, or 20 micron pitch, and a frame rate in excess of 5 frames per second, and more preferably greater than 10, 15, 20, and 25 frames per second. In a preferred embodiment, a light measuring device has a focal plane of greater than 75,000 pixels, less than a 20 micron pitch, and a frame rate in excess of 25 frames per second.

In a preferred embodiment, the light measuring device is an Indium Antimonide (InAs), Mercury Cadmium Telluride (MCT), Platinum Silicide (PtSi), Arsenic-doped Silicon (Si:As), Indium Gallium Arsenide, or CCD camera. In a preferred embodiment the light measuring device is an Indium Gallium Arsenide camera, and even more preferred a SU320-1.7RT-D/RS 170 camera from Sensors Unlimited Inc. (Sensors Unlimited Inc., 3490 US Rte 1, Building 12, Princeton, N.J., 08540), which is capable of receiving light at 76,800 pixels.

The datapoints are capable of outputting a signal. As used herein, "outputting a signal" means the production of any form of signal that can be used to directly or indirectly measure the intensity of the light on one or more datapoints. For example, the signal can be produced through conversion of light energy into electrical impulses, or otherwise.

Particular outputs can be correlated with a trait. Based on such a correlation, whether a seed exhibits a trait can be determined. In a preferred embodiment, known information has been gathered though conventional methods and correlated with the measurements. For example, a seed can be analyzed with the method of the present invention in order to produce a known set of measurements. The actual concentration of chemical components can then be measured with conventional chemometric techniques, and the resulting values can be associated with the measurements produced with the present invention. The process is repeated for seeds with varying chemical composition, thereby creating a set of associations. When an unknown seed is then analyzed with the method of the present invention, the measurements produced by the datapoints can be compared to the known set of associations to predict the composition of the seed, and the predicted composition of the seed can be compared to a predefined threshold to determine whether the seed exhibits the trait. As used herein, "exhibits a trait" means the measurements from the datapoint array are above a minimum value, below a maximum value, or within a range, any of which can be predefined. The values can correspond to measurements from any wavelength or any combination of wavelengths.

For any given trait, the measurements of one or more wavelengths of light can be used to determine whether a seed exhibits a trait. Since the spectrograph will disperse light onto the datapoints in a known pattern, datapoints can be associated with the wavelengths, and measurements from those datapoints can likewise be associated with the wavelengths.

In a preferred embodiment, determining whether a seed exhibits a trait relies on multiple wavelengths. Such a multivariate determination can comprise up to the entire set of wavelengths entering a light measuring device. In such an embodiment, light in the wavelength range of 800 to 2,600 nanometers can be used, more preferable 800 to 2,200 nanometers. When a seed is examined with multiple wavelengths, such wavelengths will form a profile. A profile is the combined set of signals for a seed, any portion of a seed, or more than one seed. For example, in a single seed analysis, the signals from datapoints representing an entire seed can be combined into a profile. The datapoints associated with a portion of the seed, for example the endosperm, can be combined to form a profile for the endosperm. For a bulk sample, in one embodiment, the datapoint signals can be averaged or otherwise combined to form a profile for the entire sample. In a preferred embodiment, profiles can be correlated with a particular trait.

In another preferred embodiment, determining whether a seed exhibits a trait uses one or several distinct wavelengths associated with the presence of a particular trait. The table below lists several wavelengths that can be associated with particular traits and can be used to predict the correlated traits.

| Trait | Wavelength, in nanometers |
|---|---|
| Lignin | 2,270 |
| Oil | 2,310, 1,274, 1,284, 1,318, 1,410, 1,510, 1,772, 1,790, 2,136, 2,245, 2,250 |
| Cellulose | 2,336 |
| Protein | 2,180, 1,460–1,530, 1,680, 1,709, 2,083, 2,139, 2,180, 2,190, 1,282, 2,110, 2,388, 2,442, 1,460, 1,760, 1,574, 1,610, 1,786, 1,818, 2,084, 2,100, 2,164, 2,254, 1,018 |
| Carbohydrate | 2,100, 1,450, 1,540, 920, 1,000 |
| Moisture | 1,940, 970, 958 |
| Acid Detergent Fiber | 1,666, 1,492, 1,854, 1,558, 1,898, 2,148, 2,210, 2,250, 1,458 |
| Neutral Detergent Fiber | 2,294, 2,072, 1,902, 2,204, 1,850, 1,586 |
| Hydrated Starch | 1,000 |
| Insect Infestation | 1,000–1,350, 1,500–1,680 |
| Shape or Breakage | 1,104, 1,300 |
| Germ | 2,180, 1,460–1,530, 1,680, 1,709, 2,083, 2,139, 2,180, 2,190, 1,282, 2,110, 2,388, 2,442, 1,460, 1,760, 1,574, 1,610, 1,786, 1,818, 2,084, 2,100, 2,164, 2,254, 1,018, 2,310, 1,274, 1,284, 1,318, 1,410, 1,510, 1,772, 1,790, 2,136, 2,245, 2,250 |
| Endosperm | 2,100, 1,450, 1,540, 920, 1,000, 1,940, 970, 958 |

Other plant tissues or agricultural samples can be substituted for seeds. As used herein, plant tissues include, but are not limited to, any plant part such as leaf, flower, root, and petal. As used herein, agricultural samples include, but are not limited to, plant tissues such as seeds, but also include non-plant based material such as non-organic matter or non-plant based matter that occur in an agricultural context. Fungal samples are an example of an agricultural sample.

Individual seeds or batches of seeds can be utilized with the methods and devices of the present invention. A batch of seeds is any number of seeds greater than one. As used herein, a "member" of a batch is any single seed within the batch. A batch of seeds can be defined by number. In a preferred embodiment, a batch of seeds is greater than 10 seeds, more preferably greater than 20, 50, 500, 1,000 or 10,000 seeds. In another embodiment the batch of the seeds may be classified by its origin, such as seeds that are derived from a single ear, single plant or single plant cross.

The individual seeds in a batch can be simultaneously analyzed with a method of the present invention. As used herein, "simultaneously" means any set of data that derives from a single analysis. A single analysis can be a single line scan of a sample, or multiple line scans of a sample. For example, an analysis of a single bulk sample line by line constitutes a single analysis. Such simultaneous analysis can be the simultaneous analysis of a batch of seeds for one or more traits. Such simultaneous analysis can also be the simultaneous analysis of a seed for multiple traits. In a preferred embodiment, more than one trait can be analyzed simultaneously. In a more preferred embodiment, more than 3, 4, 5, or 6 traits can be analyzed simultaneously. In an even more preferred embodiment, between 5 and 10 or between 10 and 20 traits can be analyzed simultaneously.

In one embodiment, the seeds from a single source are provided together in the sampling device. In one embodiment the single source can be any source that provides seeds having a common genetic background, such as an ear of corn, a single plant, or the product of a single cross. Using this method, seeds from the batch are provided as a randomly provided group in the sampling device. As used herein, "randomly providing" a batch of seeds in a sampling device means disposing the seeds in the sampling device without regard to orientation or separation of seed at a later time. For example, a batch of 100 seeds that is poured into a large, single cuvette for analysis is said to be "randomly provided."

After signals are outputted, software programs such as edge detection programs, for example Matlab version 5.3 with Image Processing Toolbox, by Mathworks Inc. (Mathworks Inc., 24 Prime Park Way, Natick, Mass. 01760) and ENVI version 3.2, by Research Systems Inc. (Research Systems, Inc., 4990 Pearl East Circle, Boulder, Colo. 80301), can then be used to analyze the signals outputted by the datapoints to determine the datapoints that correspond to individual seeds. These datapoints can then be associated with those individual seeds. As used herein, "associating" members with "corresponding datapoints" means assigning the measurements from a group of contiguous datapoints as attributable to one member of the batch for purposes of determining whether a trait is present.

In another embodiment, seeds in a batch are provided in a sampling device that is capable of maintaining each seed in its own individual compartment. An "individual compartment" as used herein can be anything that can position each seed so that the seed can be associated with datapoint measurements after analysis. In one embodiment the sampling device comprises a flat surface and is disposed horizontally, and the individual compartments are designated portions of the flat surface. In another embodiment, the sampling device comprises individual compartments having a floor and four walls arranged in a square pattern into which individual seeds can be provided. In yet another embodiment, the sampling device is a flat surface upon which is removably positioned individual compartments having only four walls. In this embodiment, either the flat surface or the individual compartments can be removed to allow sorting of the seeds.

In any of the embodiments above for batch analysis, the time to perform the method for the entire batch can be less than 30 seconds, preferably less than 10 seconds, and more preferably less than about 5 seconds. This reduced sampling time improves throughput of samples relative to the prior art, and allows greater screening of crop samples within one breeding cycle.

Further, in any of the single seed and batch analysis embodiments given above, the seed can be analyzed for more than one trait at a time. For example, traits corresponding to different wavelengths or ranges of wavelengths and traits that have a cumulative effect within the same range can be simultaneously investigated. Also, different tissues of an individual seed can be analyzed separately. Using spectral modeling to differentiate between the two tissues, regions of contiguous datapoints can be associated with any portion of a seed or plant tissue, such as, for example, the germ and the endosperm. The spectral data for the different portions can then be used to differentially analyze the different tissues of the seed.

For any of the embodiments listed above, the sample can be imaged with the spectrograph and light measuring device line by line. In a preferred embodiment, the light source comprises a cylindrical lens that focuses the light in a thin beam across the width of the sample. The spectrograph has an entrance slit that is aligned with the line of light on the sample, thereby maximizing the amount of reflected or transmitted light that enters the spectrograph. As used herein, a "line" of light is reflected or transmitted light that is passed through the spectrograph and that corresponds to a physical region on the sample of a specified shape. In a preferred embodiment, the specified shape is a thin rectangular shape or segment. A sample is therefore said to comprise a multitude of contiguous lines, which, when placed in their correct order, together make up the sample. As used herein, the "first line" is the line that is analyzed by the method before all other lines on the sample. In a preferred embodiment, the first line is a line at one end of the sampling device. The end of the sampling device can be any side or edge. For example, the end on a sampling device with a square shaped face can be any of the four edges of the face. A method of the present invention can be performed using a single line, or any combination of lines up to the entire complement of lines for the sample. As more lines are analyzed, more of the sample is interrogated. In one embodiment, a single line is analyzed. In another embodiment, several non-adjacent lines are analyzed. In a further embodiment, all lines of the sample are analyzed from one end of the sample to the other, starting with the first line and proceeding with subsequent lines until the last line is reached. As used herein, a "subsequent line" is the unanalyzed line adjacent to the line that has just been analyzed. The "last line" is the final line analyzed.

In order to analyze subsequent lines after the first line, a sample can be moved the thickness of a line in order to align each subsequent line relative to the light source and the spectrograph. This relative movement can be accomplished by moving either the sampling device or the light source and spectrograph. In a preferred embodiment the sampling device is mounted on a linear translational stage that is capable of being moved either in increments equivalent to the width of one line, or at a constant velocity. In another preferred embodiment, the stage is moved at a constant velocity, and a light measuring device is controlled so as to capture an image at the exact time when each subsequent line, without overlap, is aligned with the slit. By analyzing the first line and each subsequent line, an entire sample can be analyzed.

Methods and devices of the present invention can be used in a breeding program to select plants or seeds having a desired trait. In one aspect, the present invention provides a method for selecting a seed having a trait, comprising: (A) providing the seed in a sampling device; (B) directing light from a light source to the seed, thereby forming reflected light and transmitted light; (C) passing the reflected light or the transmitted light through a spectrograph to form dispersed light; (D) receiving the dispersed light in a light measuring device comprising an array of multiple datapoints; (E) outputting a signal for each of the multiple datapoints with the light measuring device; and, (F) determining whether the seed exhibits each of the traits based on the signals.

In another aspect of the present invention, it provides a method of introgressing a trait into a plant comprising using comprising: (A) providing the seed in a sampling device; (B) directing light from a light source to a seed and generating transmitted or reflected light; (C) passing the transmitted or reflected light through a spectrograph; (D) receiving the transmitted light or reflected light in a light measuring device comprising an array of multiple datapoints; (E) outputting a signal for each of the multiple datapoints with the device; (F) determining whether the seed exhibits the trait based on the signals; (G) selecting the seed having the trait based on the signals; (H) growing a fertile plant from the seed; and, (I) utilizing the fertile plant as either a female parent or a male parent in a cross with a second plant.

The methods of introgression and selection of the present invention can be used in combination with any breeding methodology and can be used to select a single generation or to select multiple generations. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include, but are not limited to, pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new soybean cultivars entails the development and selection of soybean varieties, the crossing of these varieties and selection of superior hybrid crosses. The hybrid seed can be produced by manual crosses between selected male-fertile parents or by using male sterility systems. Hybrids are selected for certain single gene traits such as pod color, flower color, seed yield, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, for example, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

In one embodiment the present invention is used to differentiate haploid samples from non-haploid samples. The use of haploid plants increases the efficiency of recurrent selection in plant breeding programs by providing a way to produce completely homozygous lines of doubled haploid lines. Because haploids are hemizygous, i.e., only one allele per locus, they are useful for mutation studies and selecting against undesirable recessive alleles. Methods of the present invention can be used to discriminate haploid samples from other types of samples, such as diploids. Any haploid trait that produces a phenotype that produces reflected or transmitted light that has a different spectral composition than a non-haploid sample can be determined with the methods of the present invention. For example, some parental lines carry marker genes such as R-nj, which enable haploids to be identified at the stage of mature seeds by the anthocyainin coloration of the top of the endosperm and the lack of coloration in the embryo. Methods of the present invention can readily discern the presence or absence of these phenotypes at the required location on the seed.

Descriptions of other breeding methods that are commonly used for different traits and crops can be found in one of several reference books (e.g Fehr, *Principles of Cultivar Development* Vol. 1, pp. 2–3 (1987)), the entirety of which is herein incorporated by reference).

Analytical Devices and Systems

The present invention provides a device for measuring properties of agricultural products, comprising: a processing device for producing a sample; a sampling device for providing a sample, wherein the sampling device is disposed to receive the sample from the processing device; and, an optical spectroscopic imaging system, wherein the system is disposed to analyze the sample in the sampling device. The present invention also provides a device for measuring properties of agricultural products, comprising: a sampling device for providing a sample; an optical spectroscopic imaging system, wherein the system is disposed to analyze the sample in the sampling device; and, a sorting device for sorting the sample into two or more different groups, wherein the sorting device is disposed to receive the sample from the sampling device. The present invention further provides a device for measuring properties of agricultural products, comprising: a processing device for producing a sample; a sampling device for providing a sample, wherein the sampling device is disposed to receive the sample from the processing device; an optical spectroscopic imaging system, wherein the system is disposed to analyze the sample in the sampling device; and, a sorting device for sorting the sample into two or more different groups, wherein the sorting device is disposed to receive the sample from the sampling device.

The device described herein utilizes an optical spectroscopic imaging system to analyze agricultural samples. As used herein, an "optical spectroscopic imaging system" is any system that can form an image of a sample, wherein the image comprises a multitude of datapoints. In a preferred embodiment, the optical spectroscopic imaging system comprises a light source, a device for dispersing light, and a light measuring device. As used herein, a "device for dispersing light" means any device that is capable of dispersing light having mixed wavelengths into separate wavelengths. In a preferred embodiment, the device for dispersing light is a spectrograph. The light source, spectrograph, and light measuring device include, but are not limited to, those described herein.

A sample can be prepared for analysis with a spectroscopic imaging system with a processing device. As used herein, a "processing device" is any device that is capable of separating the desired portion of a plant from rest of the plant. In a preferred embodiment, the processing device is a sheller, a thresher, or a combine. The sheller can be, for example, an Almaco modified single ear corn sheller (Almaco, 99 M Avenue, P. O. Box 296, Nevada, Iowa 50201).

After the sample is prepared with the processing device, it is analyzed with the spectroscopic imaging system. After analysis with the spectroscopic imaging system, the sample can be automatically sorted with a sorting device.

As used herein, a "sorting device" is any device that is capable of separating the sample into at least two different bins depending upon the results of the analysis. A sorting device can be, for example, a single movable vane that directs the sample in one of two directions. In a preferred embodiment, a sorting device is capable of independently sorting 10, 20, 50, or 100 individual seeds. As used herein, a "bin" is any device that can hold a portion of a sample separate from other portions.

In a preferred embodiment, the sorting device is capable of sorting a single batch of seeds into one of a multiple of bins. This type of sorting is useful if more than a single trait is being examined during analysis.

In a preferred embodiment, a processing device and a sorting device are coupled to a sampling device and a spectroscopic imaging system to provide a device for automatically providing a sample, analyzing a sample, and sorting a sample. In a preferred embodiment, a sample can be provided, analyzed, and sorted faster than once every 10 seconds, more preferably faster than once every five seconds.

FIG. 1 represents a schematic diagram of one embodiment of the device of the present invention generally at 10. A light source 12 is disposed so as direct light at the sample 14 in the sampling device 16, which is positioned so as to reflect light to a light measuring device 18. The light source 12 can be any device that is capable of providing light of the correct wavelength range to the sample 14 for analysis by the light measuring device 18. The sampling device 16 can be any device that is capable of providing a sample 14 for analysis by holding and positioning the sample 14 in the viewing field of the light measuring device 18. The light measuring device 18 can be any device that is capable of characterizing the intensity of one or more wavelengths of interest of the light from the sample 14.

FIG. 1 a is a schematic representation of a preferred light measuring device 18 and attachments shown generally at 20. Attached to the light measuring device 18, which in this embodiment is a progressive scan camera 22, is an imaging lens 24, and a straight axis imaging spectrograph 26. The components are arranged so that light coming from the sample 14 first passes through the imaging lens 24, then passes through the spectrograph 26 before entering the camera 22. An electronically actuated shutter 38 is located on the front of the imaging lens. When closed, the shutter 38 completely blocks any light from entering the spectrograph, and is used to collect a dark image for use in correcting the samples images collected with the system.

The imaging lens 24 can be any conventional video lens, such as an Electrophysics 25 mm f/1.4 macro lens with integral iris diaphragm. The imaging lens 24 couples the reflected or transmitted light from the sample 14 into the straight axis imaging spectrograph 26, which is, in one embodiment, a Specim Inspector N17–04-100 with a slit width of 80 microns. The spectrograph 26 has a nominal spectral range of 900 to 1,750 nanometers, a nominal spectral resolution of 10 nanometers, and a numerical aperture of f/2.8. The spectrograph is based upon a prism/grating/prism (PGP) dispersing element and transmissive optics, which provide a straight optical axis, an astigmatism free image, and a polarization independent through-put. The spectrograph 26 is, in one embodiment, equipped with a standard C-mount flange that allows direct connection to the imaging lens 24 and the focal plane array camera 22, thereby converting the camera 22 into a spectral line imaging system.

Figure 1A:
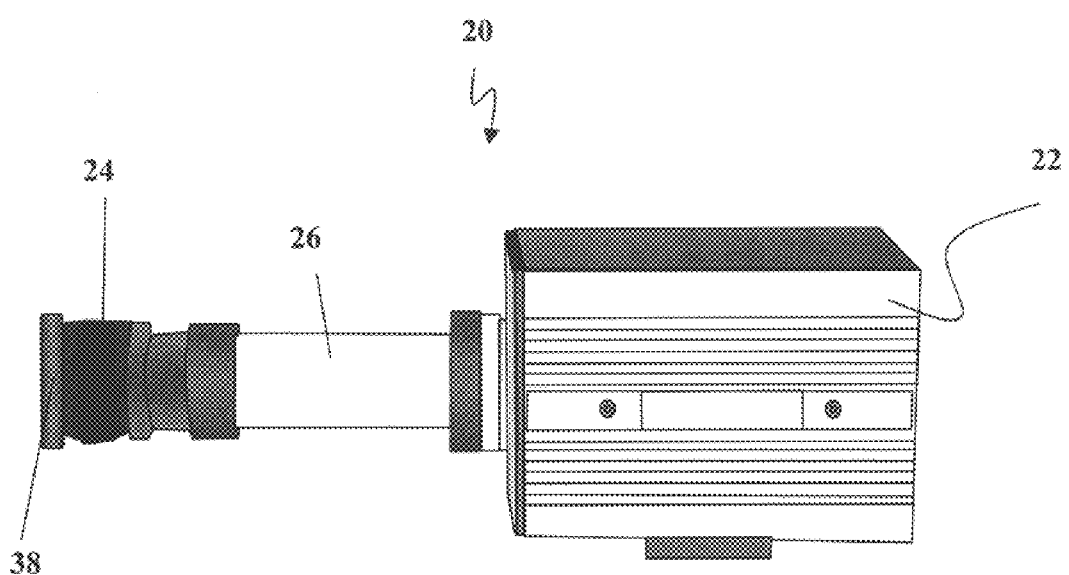
FIG. 1a is a schematic diagram of one embodiment of a light measuring device, where the light measuring device is a spectrometer.

The focal array progressive scan camera 22 shown in FIG. 1a can be, for example, Indium Antimonide (InAs), Mercury Cadmium Telluride (MCT), Platinum Silicide (PtSi), Arsenic-doped Silicon (Si:As), and Indium Gallium Arsenide, with Indium Gallium Arsenide preferred. An Indium Gallium Arsenide focal plane array, and may be, for example, a SU320-1.7RT-D/RS170 camera from Sensors Unlimited Inc. The format of the focal array for this camera 22 is 320 by 240 pixels for a total of 76,800 detector pixels with a 40 micron pitch for each pixel. The camera 22 has an analog to digital accuracy of 12 bits, a pixel readout rate of 6.1 MHz, and a spectral response of 900 to 1,730 nanometers. The camera 22 has a progressive scan video output allowing acquisition of one field per frame. The frame rate of the camera 22 in the progressive scan mode is 60 frames per second. This means a spectral line image can be captured every 16.67 milliseconds. In one embodiment, the 320 pixel axis of the camera 22 is used for the spatial axis while the 240 pixel axis is used for the spectral axis. This means that 320 individual spectra can be acquired every 16.67 milliseconds.

Figure 1B:
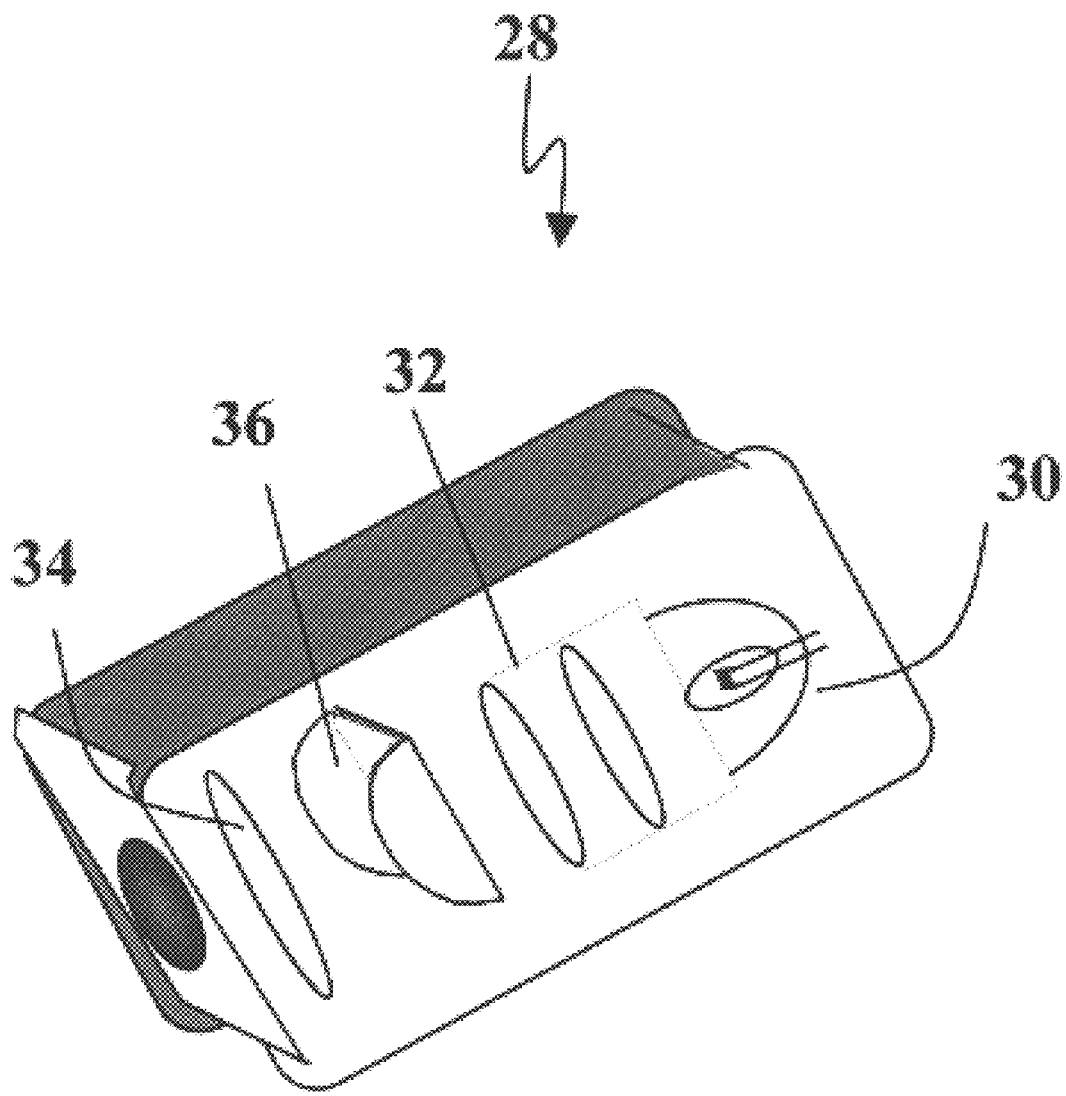
FIG. 1b is a schematic diagram of one embodiment of a light source.

Illumination of the sample 14 for spectral line imaging is, in one embodiment, accomplished with a continuous broadband source such as a quartz tungsten halogen lamp. The light source 12 can be, for example, an AS220 lamp and assembly from CVI Laser Inc. One embodiment of the light source is shown in FIG. 1b generally at 28. The source contains a thirty watt quartz tungsten halogen lamp with integral parabolic reflector 30, condenser optics 32, a near infrared cut-on filter 34, and a cylindrical lens 36 to focus the light to a line for uniform line illumination. The near infrared cut-on filter 34 removes unwanted, harmful ultra-violet and visible light from impinging upon the sample.

Figure 1C:
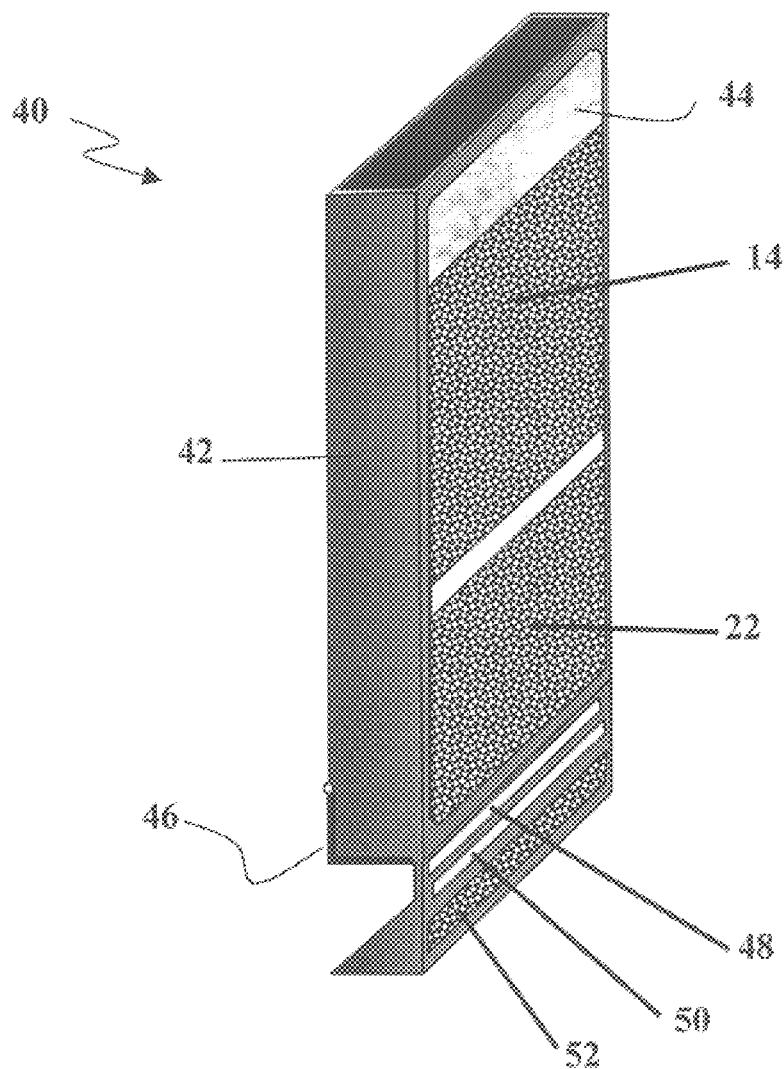
FIG. 1c is a schematic diagram of one embodiment of a sampling device.

One embodiment of a sampling device 16 is shown in FIG. 1c generally at 40. In FIG. 1c, the sampling device is a cuvette, which consists of a rectangular compartment 42 with a quartz window 44 through which the sample 14 is imaged, a bottom door 46 to remove the sample 14 after analysis is complete, a strip of a calibrated reflectance material 48, for example Spectralon from Labsphere Inc. (Labsphere, Inc., Subsidiary of X-Rite, Inc., Shaker St., PO Box 70, North Sutton, N.H. 03260-0070), to normalize the instrument response, a strip of calibrated reflectance material doped with rare earth oxides 50 for establishing the accuracy of the wavelength scale, and a smaller sample compartment 52 with its own quartz window disposed at the bottom of the cuvette to hold a reference sample of the same type of agricultural product as the one being analyzed.

Figure 2:
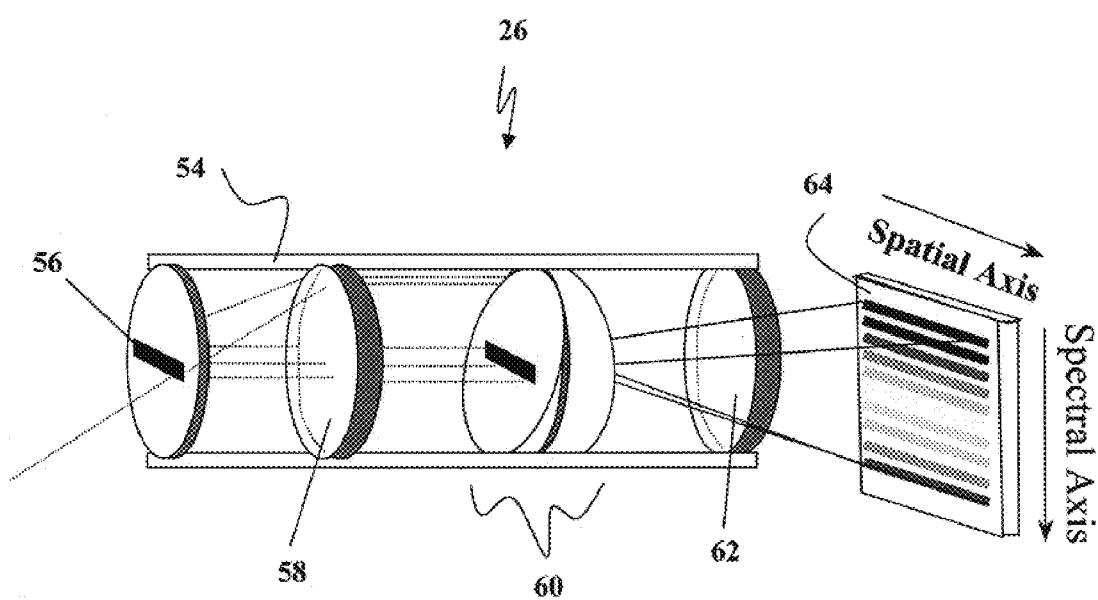
FIG. 2 is a schematic diagram of one embodiment of a straight axis prism/grating/prism imaging spectrograph.

The tubular, opto-mechanical construction of the spectrograph in FIG. 1 is shown generally in FIG. 2 at 26. The spectrograph 26 is compact, stable, rugged, and has no moving components. The grating in the PGP component is a volume-phase transmission grating that provides a good diffraction efficiency over a broad range. For one embodiment of the present invention, the diffraction efficiency characteristics are a maximum of greater than 60% at 1,100 nanometers and an efficiency of 40% at 1,700 nanometers. Direct sight transmissive optics produce a high quality image with a short focal length and fast optics, thus minimizing the spectrograph size while providing good light collection efficiency. The spectrograph 26 comprises a tubular housing 54 within which is disposed a disc 56 defining an entrance slit. Light from the sample 14 enters through the entrance slit and passes through a lens 58, which focuses the light onto the PGP component 60 where it is dispersed to its continuous spectral distribution perpendicular to the line image. The dispersed light then passes through a second lens 62 and is focused on the focal plane array 64 of the camera 22. The central wavelength of the full spectral range goes straight through and the shorter and longer wavelengths are dispersed symmetrically on both sides of the central wavelength. The focal plane array camera 22 placed at the focus of the output of the spectrograph records in one frame the spatial line image and the spectral distribution of each pixel in the line image.

The slit width of the spectrograph 26 affects both the spectral resolution and image line width. In one embodiment, the slit is an 80 micron slit, which provides a nominal spectral resolution as defined by the full width half maximum criteria of 10 nanometers across the spectral range of 900–1,530 nanometers, while increasing to 13 nanometers at the upper spectral limit of 1,750 nanometers. The image line length and width are determined by the slit length, the slit width, lens focal length, and distance between the sample and lens. For example, a slit length of 9.9 mm, a slit width of 80 microns, a lens focal length of 25 mm, and a distance between the sample and lens of 214 millimeters gives an image line width of 0.37 millimeters and an image line length of 85 millimeters.

In order for the camera 22 to measure light data from the entire contents of the sample 14, the sample 14 is moved relative to the spectrometer. The sampling device 16, the light measuring device 18, or both can be moved in order to achieve this relative movement. In a preferred embodiment, the sampling device 16 is mounted to a movable stage. The stage can be, for example, a servo controlled linear translational stage such as a Parker Hannefin Gemini GV Series with controller (Parker Hannifin Corp., 6035 Parkland Boulevard, Cleveland, Ohio). The linear translational stage moves the sample cuvette precisely and reproducibly, at a constant velocity through the field of view of the imaging spectrometer 20. The movement of the linear translational stage is synchronized with the operation of the camera 22 so that each frame captured by the camera 22 is an adjacent, non-overlapping image line of the sample. The spectroscopic image of the sample 14 in the cuvette is formed by appending adjacent, non-overlapping image lines on the sample together, thereby building up the image line by line.

Figure 3:
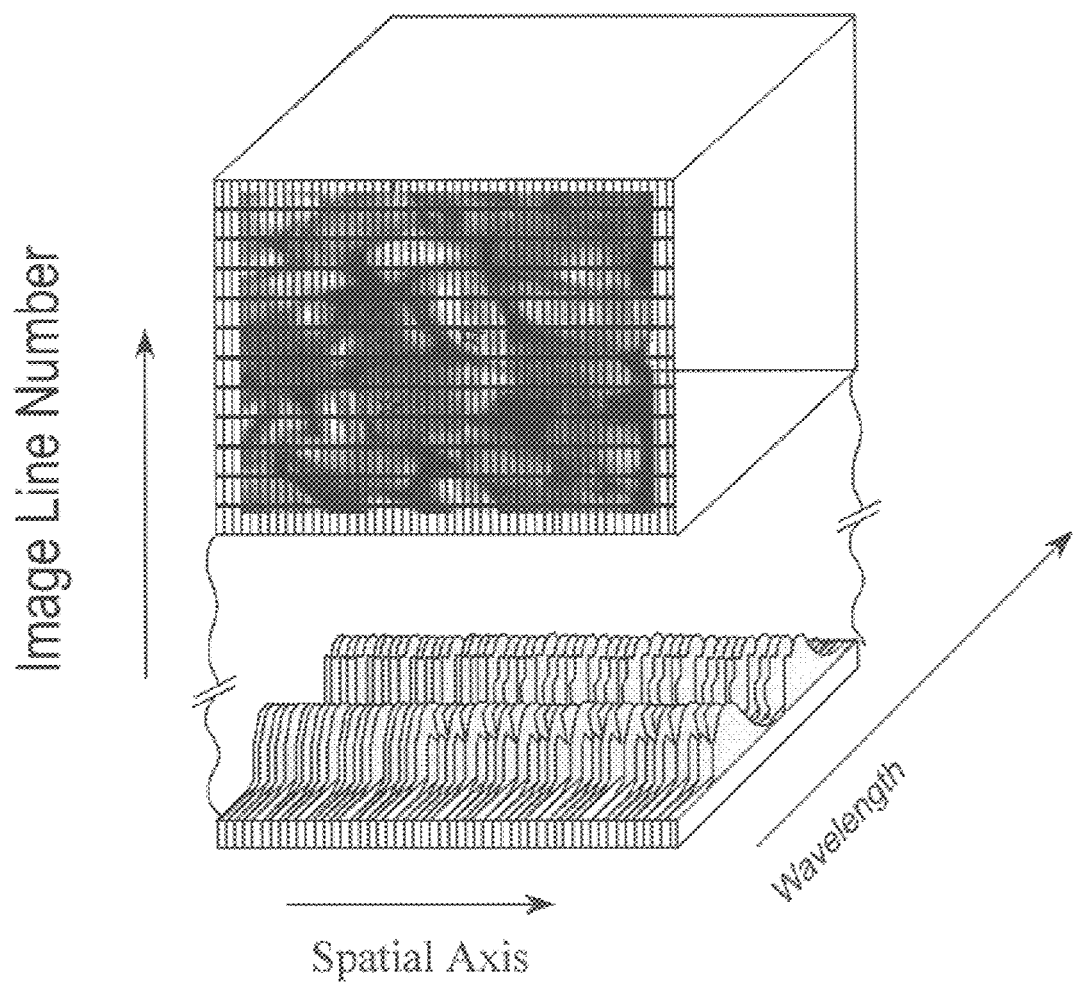
FIG. 3 is a schematic diagram of a data set.
Figure 4:
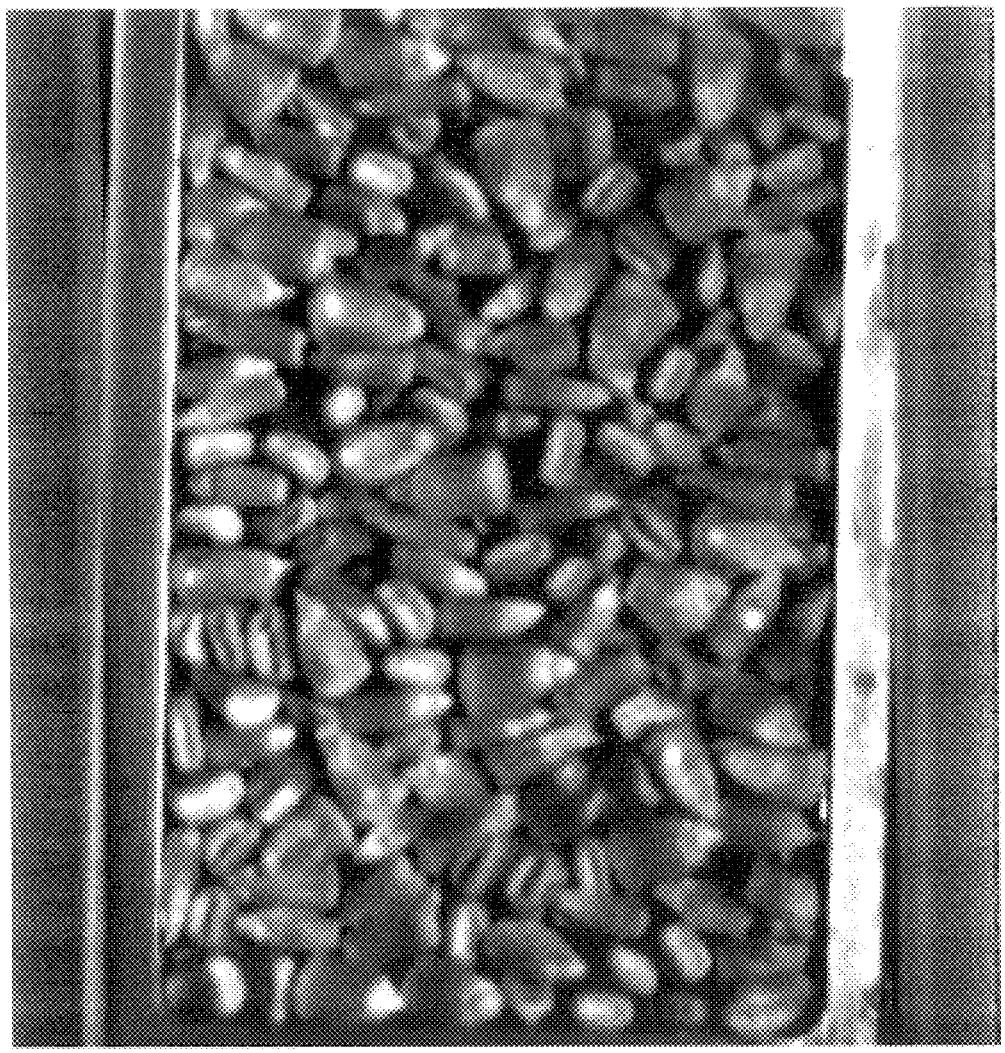
FIG. 4 is an image of a corn sample.

FIG. 3 pictorially represents the hyperspectral data cube thereby produced. As shown in FIG. 3, one dimension of the camera 22, the spatial axis, records an intensity image of each line at a given wavelength, and the other dimension, the spectral axis, records the spectral information for each image pixel. In one embodiment, the long axis of the focal plane array of the camera with 320 pixels is used for the spatial axis while the short axis with 240 pixels is used for the spectral axis. If an improvement in the signal-to-noise of the system is desired or if speed of acquisition is of primary importance, the individual pixels from each line each with a unique spectrum maybe averaged, thereby forming one spectrum per image line. For the above-described embodiment, this means that 320 spectra can be averaged every 16.67 milliseconds for each image line. In addition, a pseudo color image may be extracted from the hyperspectral data cube by assigning 3 gray-scale spectral images at unique wavelength planes to the Red Green Blue (RGB) color components, thereby producing a pseudo-color image, as shown in FIG. 4.

In the case of reflectance the light source is positioned on the same side of the sampling device 16 as the camera 22, as shown in FIG. 1. The angle between the camera 22 and the light source 12 is determined by optimizing the collection of the diffusely scattered light from the sample 14. Light is focused onto the sample 14 through the cylindrical lens 36.

Diffusely scattered light from the sample surface is directed via the imaging lens 58 into the entrance slit of the spectrograph where the transmission grating 60 disperses the light into its continuous spectral distribution perpendicular to the image line defined by the input slit. The central wavelength of the design wavelength range goes straight through, and the shorter and longer wavelengths are dispersed symmetrically on both sides of the central wavelength.

The various embodiments described above for the light source 12, sampling device 16, and light measuring device 18 can be combined with processing devices that separate different parts of plants, and sorting devices, which are capable of sorting the sample based on the light measuring device 18 output.

Figure 5:
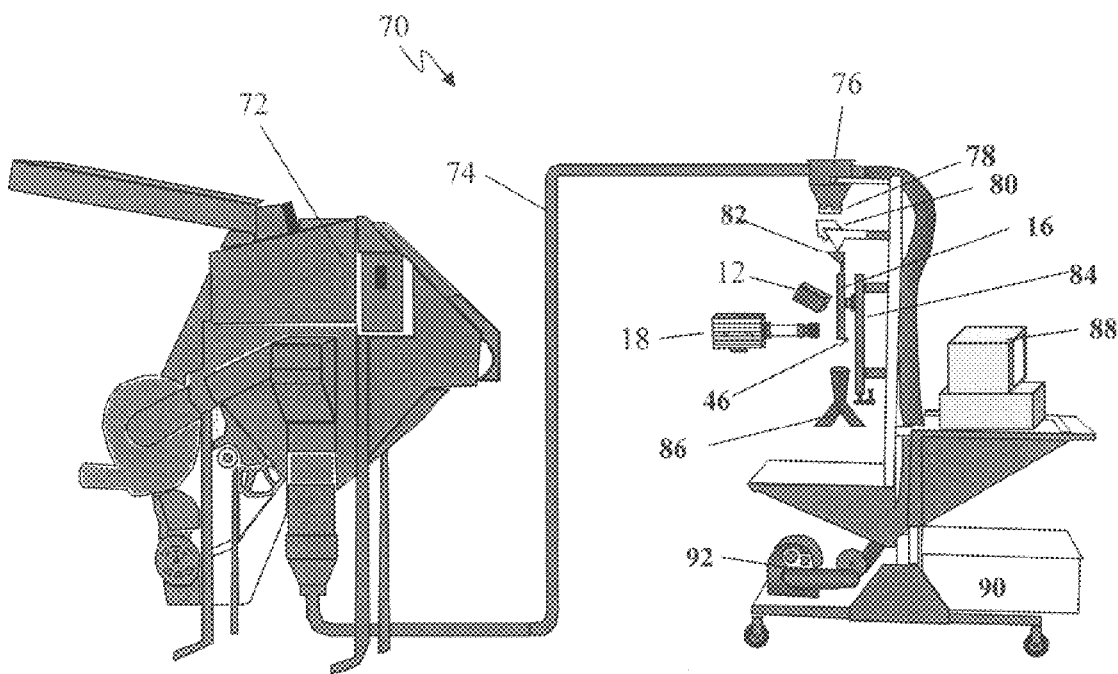
FIG. 5 is a schematic diagram of one embodiment of an automated device for providing, analyzing, and sorting bulk seed sample.

FIG. 5 shows a schematic diagram of any of the embodiments described above integrated with a conventional agricultural processing device, which in this embodiment is a sorting device, and a control system generally at 70. The output of a processing device 72 is connected by a tube 74 to a sample inlet chute 76. The processing device 72 can be any conventional agricultural device that separates the desired part of the plant from the rest of the plant. In one embodiment, the processing device 72 is a single ear corn sheller, which is used to remove the corn kernels from the cob. A single ear corn sheller is designed to separate the kernels from the cob, aspirate the kernels to remove any small undesirable debris, collect the kernels in a collection compartment, and eject the cob after shelling. The output of the processing device 72 is fed directly through a tube 74 into a sample inlet chute 76 of the test system. Movement of the sample 14 through the tube 74 is provided by a vacuum motor 92. A cyclone 78 with a door prevents the sample from leaving the cyclone 78 chamber. The door can be activated, for example, with a solenoid. When the solenoid is actuated (when the sampling device is empty and ready to receive a new sample) the door in the cyclone 78 is opened, and the sample falls into a weighing cell 80 for measuring the weight of the sample. The bottom of the weighing cell 80 is a trap door 82, which may be actuated, for example, by a solenoid. After the weight of the sample is recorded, the trap door 82 is opened, thereby allowing the sample to drop into the sampling device 16.

The sampling device 16, in this embodiment, is attached to a servo controlled linear translational stage 84, which can be controlled to move the sampling device 16 at a constant velocity through the field of view of the light measuring device 18. The stage 84 is also used to move the sampling device 16 into position to accept the next sample or to discharge the sample 14 after the measurement is complete. Images are acquired by imaging adjacent lines on the sample 14, thereby building up the image line by line. The speed at which the translational stage 84 moves the sampling device 16 is determined by the width of the image line and the readout speed of camera 22 per image frame. After the image data has been collected and the data processing is complete, the bottom door 46 of the sampling device 16 is opened, which allows the sample to fall downward. The bottom door 46 can be opened, for example, by an electronic actuator. After falling out of the sampling device 16, the sample 14 falls into a sorting device 86 where the sample 14 is mechanically directed into any one of two or more containers. In one embodiment, the sorting device 86 can comprise electronically actuated vanes that direct the sample into the containers. The processing, analyzing, and sorting combination described above can be designed as a single unit, or as separate units that can be coupled.

A control system 88 can be included to automate all of the functions of the system, including the collection of image frame data from the camera 22, movement of the translational stage 84, opening and closing of doors, movement of the sorting device vanes, and data analysis. The associated power supplies and input/output controllers are optionally contained in an electronics cabinet 90. In a further embodiment, the sorting device 86 has multiple vanes, thereby allowing sorting into greater than two containers. The sorting device 86 can be configured to accommodate sorting into tens of containers if multiple characteristics are measured at one time.

Figure 6:
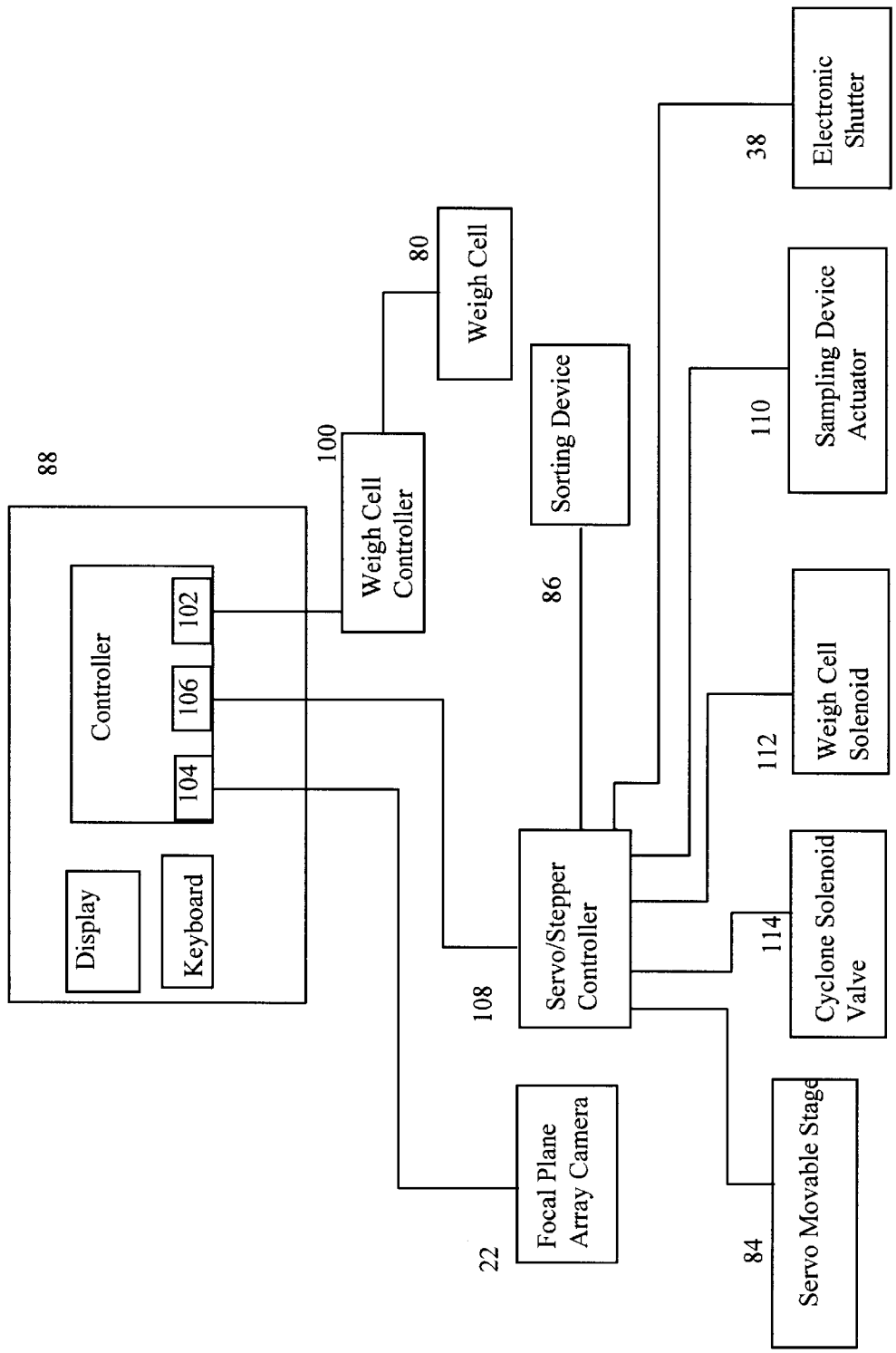
FIG. 6 is one embodiment of a block diagram of an electronic control system suitable for use in the practice of the device of FIG. 5.

FIG. 6 is a block diagram of the electronic control system suitable for use in the practice of the embodiment of the present invention. As shown in FIG. 6, in one embodiment the control system 88 comprises a controller, a display, and a keyboard. The controller contains machine readable code which controls the various components of the system using signals received from the weighing cell 80, a weigh cell controller 100, and the light measuring device 18 (through connections 102 and 104). The controller signals the various components to take appropriate actions through connection 106 and the servo/stepper controller 108, which can be any conventional servo/stepper controller, such as a 6K4 controller. The servo/stepper controller 108 controls the sorting device 86, the camera shutter 38, sampling device actuator 110, the weigh cell door solenoid 112, the cyclone solenoid valve 114, and the movable stage 84.

As will be seen by those of skill in the art, various controller configurations and machine readable code can be used to effectuate the desired automated control of the system.

In one embodiment, the system functions as follows. After a sample 14 is received in the cyclone 78, the sample 14 is aspirated to remove excess debris. The movable stage 84 moves the sampling device 16 to its "home" position just below the Spectralon reflectance reference material 48 where the system waits to begin acquiring the imaging data. An electronic shutter 38 blocks the entrance to the light measuring device 18. The control system 88 acquires and stores a dark image for later calculation of the sample reflectance. The electronic shutter 38 is then opened. The movable stage 84 accelerates the sampling device 16 until it reaches its pre-programmed constant velocity moving it through the field of view of the light measuring device 18. The start of the movement of the stage 84 triggers the acquisition of image frames from the light measuring device 18 to the control system 88. Spectroscopic images are acquired by imaging adjacent lines on the sample, thereby building up the image line by line. The speed at which the movable stage 84 moves the sampling device 16 is determined by the width of the image line and the readout speed of the light measuring device 18 per image frame. Acquisition and storage of a dark image and a reflectance reference target with each sample assures correct compensation by the system for any offset due to dark current in the detector, lighting spatial non-uniformity across the scene line, and light source color temperature drift. The control system continues taking image frames as the movable stage 84 moves. The control system 88 stops acquiring image frames and stops the motion of the stage when a valid "End of Scan" criteria is encountered in the control system. The logical expression "End of Scan" is tested after each image frame is acquired. The total number of valid image lines is proportional to the total volume of the sample. The volume of the sample along with the weight data from the weighing cell is used to calculate the yield. After the image data has been collected and the data processing is complete, the sample 14 is sorted as before depending upon the pre-determined selection criteria and the analysis of the light measuring device 18 data.

Quantitative chemical information for the sample can be extracted from the spectral data collected with the present invention. It is well known that polyatomic organic molecules contained in biological materials exhibit absorption transitions in the infrared and near infrared spectral regions and these transitions are well correlated with the organic functional groups. Specifically, in the near infrared region of 770 to 2,500 nanometers, overtones and combination bands of the fundamental vibrational frequencies of the organic functional groups of O—H, C—H, and N—H provide a molecular spectral signature to correlate the concentration of chemical components.

Figure 7:
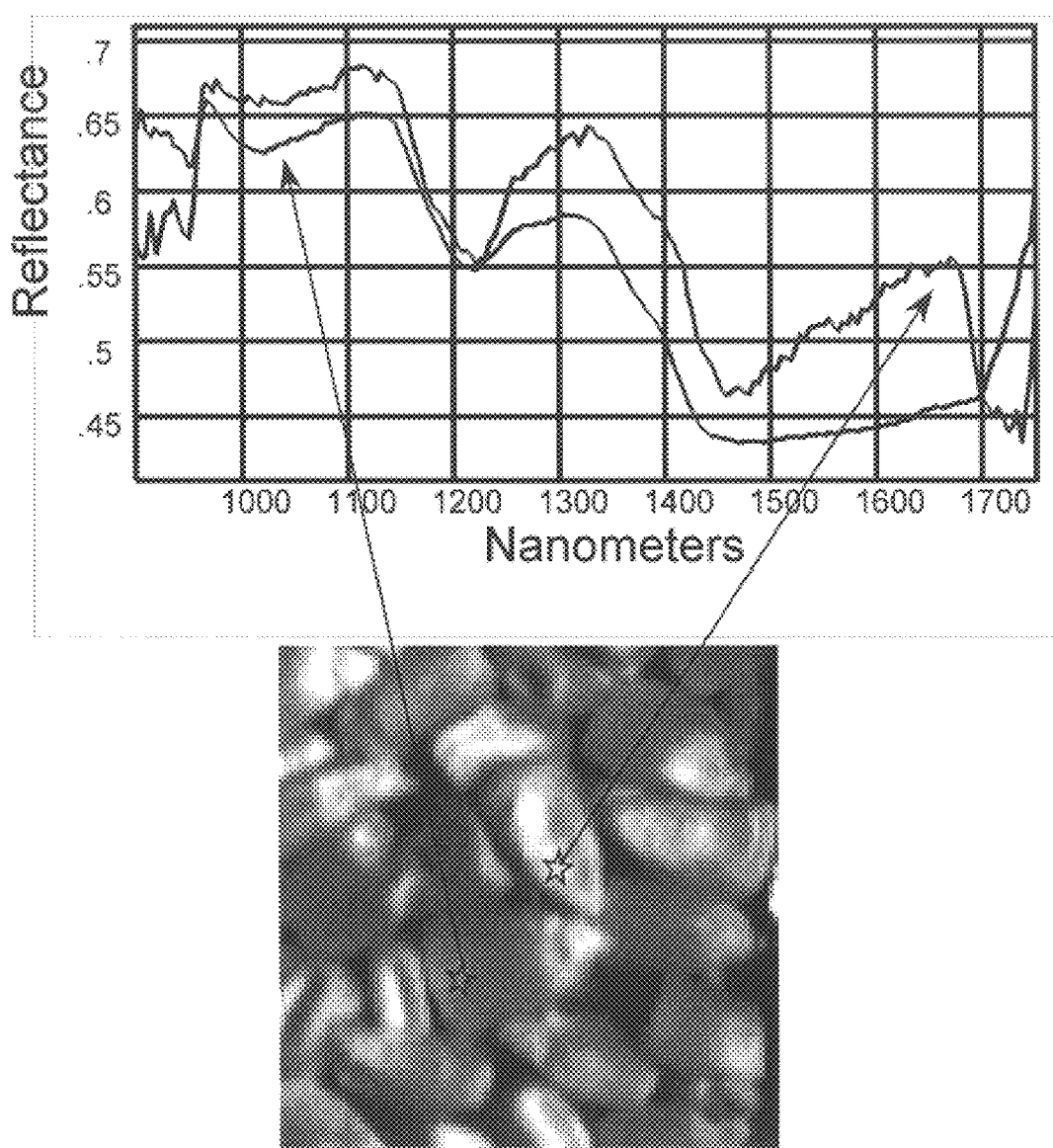
FIG. 7 is an example of an expanded gray-scale image of a bulk corn sample at 1,100 nanometers.

When used as a spectral imaging system, the present invention provides many advantages. Because light reflected from every unit of the sample within the field of view of the system is collected and measured, more accurate data can be obtained for bulk grain samples. FIG. 7 shows the type of detail that can be acquired with the preferred embodiment of the present invention. FIG. 7 shows an expanded gray-scale image of a bulk corn sample at 1,100 nanometers. Also shown are two overlaid spectra, one corresponding to a spatial point in the germ portion of a corn kernel as indicated in the image, while the other corresponds to a spatial point in the endosperm portion as indicated in the image of a corn kernel. As can be seen from the comparison of the gray-scale image along with the spectra, the two kernels can be discriminated from each other using their spectral signatures. Analysis of the spectroscopic images can be used to classify the sample based upon, for example, without limitation, endosperm size, germ size, seed shape, seed size, seed color, seed surface texture, seed weight, seed density, seed integrity, oil content, protein content, carbohydrate content, starch content, fiber content and water content. The spatial detail provided by the sample image can be used through the use of morphological filters to estimate the total number of units for a given volume as well as the average unit shape.

Figure 8:
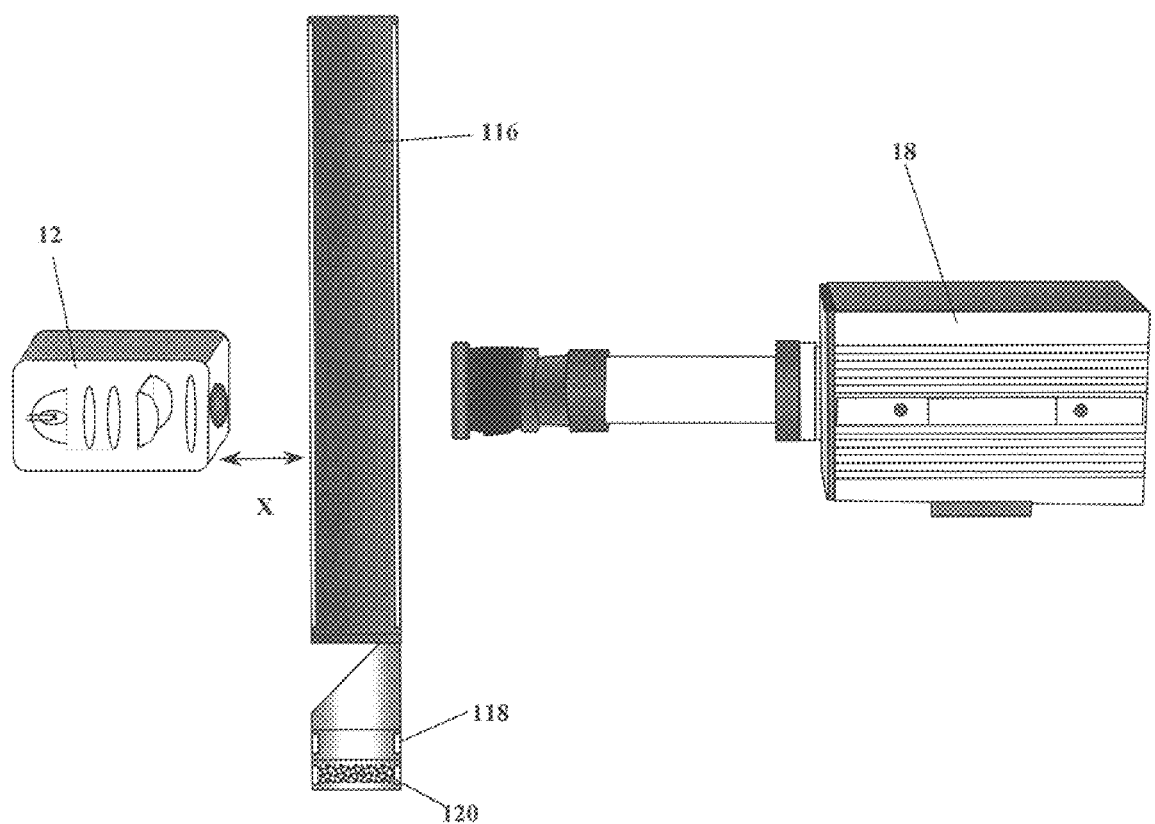
FIG. 8 is a schematic diagram of an alternate embodiment of the present invention in the form of a diffuse transmittance spectral imaging system.

Referring to FIG. 8, there is shown an alternate embodiment of the present invention in the form of a diffuse transmittance imaging system. The sampling device 116 in this embodiment allows the passage of light through two sides, and can consist of a rectangular compartment with two quartz windows through which light is transmitted through the sample to the input slit of the spectrograph 26. In the case of diffuse transmittance, the light source 12 is positioned directly opposite the light measuring device 18 at a distance X and in the same plane. Light from the light source 12 is directed into a line by the cylindrical lens and collimated through the sampling device 116 where it is focused onto the input slit of the spectrograph 26. The calibrated reference Spectralon material used in the reflectance embodiment is replaced by transmission reference cell 118 consisting of two small windows positioned on either side of the cuvette, one of which is quartz while the other is made of a neutral density filter so that a reference image may be collected. The transmittance measurement is made by dividing the image line acquired through the sample 14 by the transmission reference image. The bottom of the sampling device 116 comprises a sample cell 120 with two quartz windows on opposite sides containing a reference of the same type as being analyzed. The analytical process proceeds as before.

Figure 9:
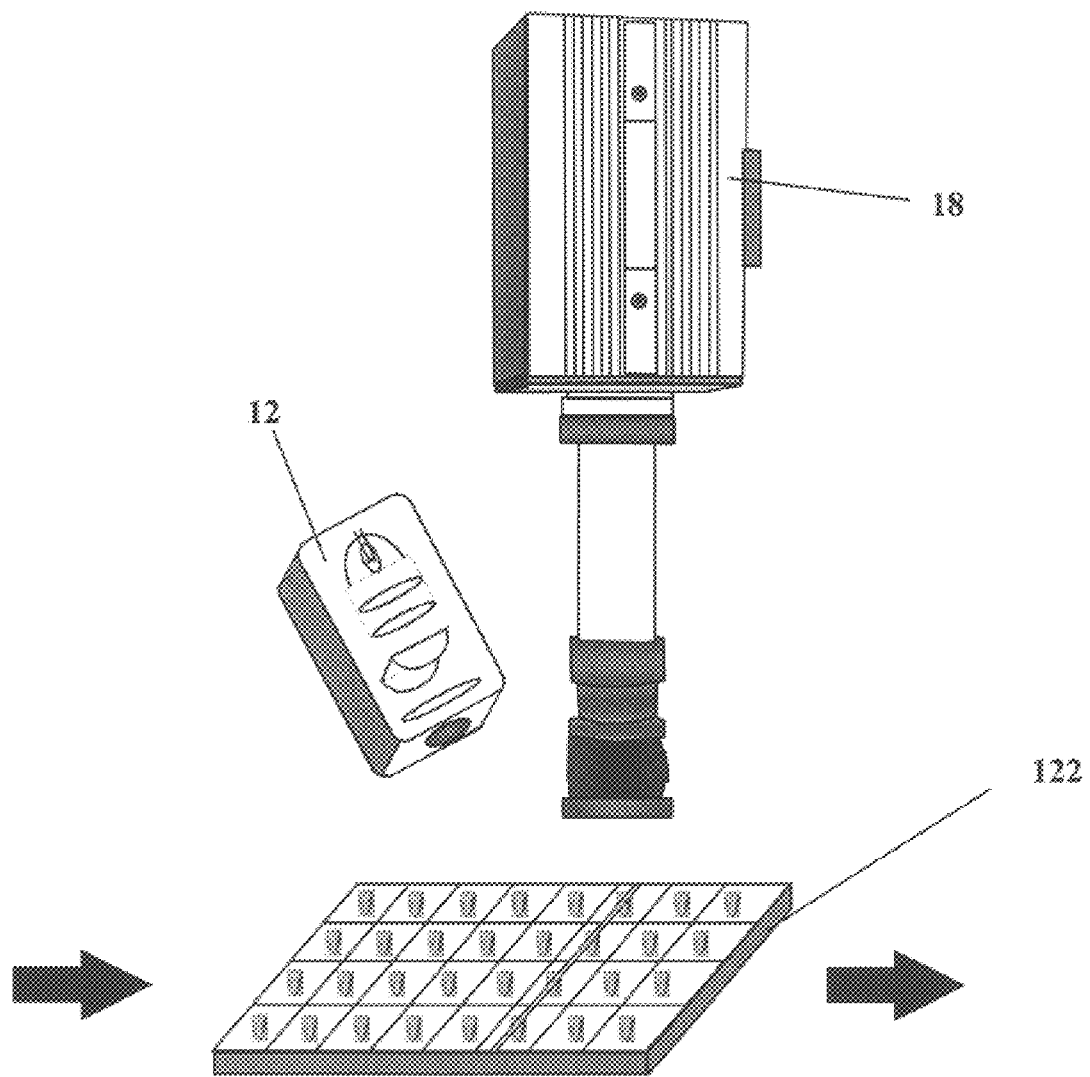
FIG. 9 is a schematic diagram of one embodiment of the present invention for single seed analysis.
Figure 10:
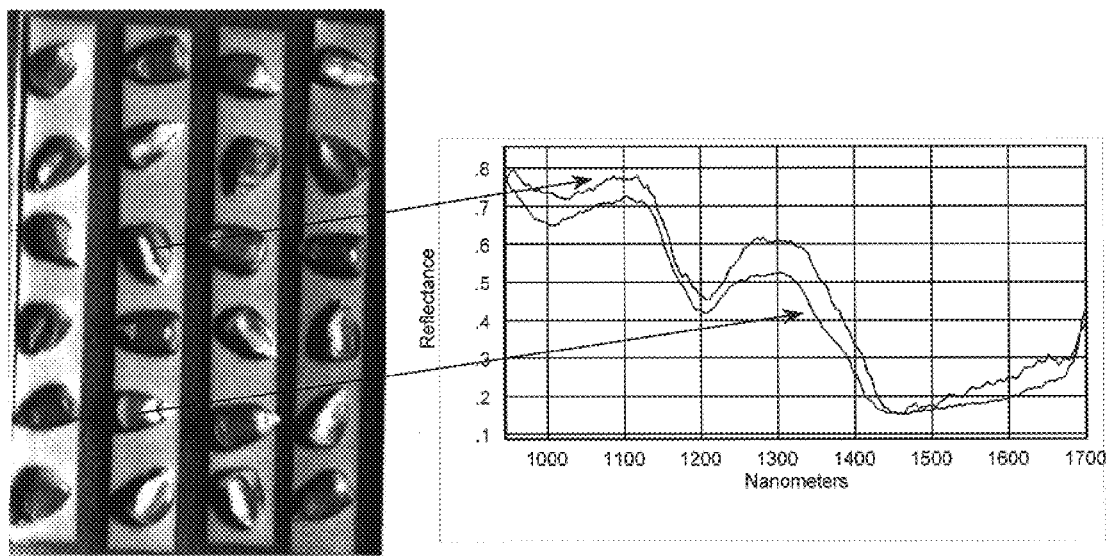
FIG. 10 shows an image of a tray of 24 corn kernels.

Referring to FIG. 9, there is shown an alternate embodiment of the present invention in the form of a diffuse reflectance system for single seed analysis. The seeds are arranged in a sampling device 122 whereby their location and identity can be maintained. Spectral images are acquired by moving the sampling device 122 at a fixed rate in a manner analogous to the system for the bulk samples. FIG. 10 shows an image of an tray of twenty-four corn kernels acquired as described above. The image was generated by selecting 3 gray scale spectral images at 3 unique wavelength planes and scaling each to either Red or Green or Blue color components. Also shown are two overlaid spectra, one corresponding to a spatial point on an individual seed in the endosperm region while the other spectrum corresponds to a spatial point in the germ region of a separate seed. The ability to differentiate between different tissues of the sample seed (for example, endosperm and germ) allows for measurement of the chosen sample characteristic in those different tissues.

The single seed analysis described above can be coordinated with a sorting device 86 that sorts each seed individually. In this embodiment, the sampling device 116 has partitions to separate the individual seeds into cells. The bottom of the sampling device 116 comprises doors that can be differentially opened to release any or all of the seeds, depending upon the programmed selection criteria. Alternatively, the sorting device 86 can comprise differentially controllable movable vanes for each cell in the sampling device 116, thereby allowing the simultaneous discharge of the seeds into the sorting device.

While the illustrated embodiments of the present invention includes spectral imaging in the near infrared spectral region, other spectral regions could be used, such as the visible, ultra-violet, or mid-infrared regions. In addition, if the light source 12 is replaced by a coherent laser, fluorescence imaging could also be performed with the present invention. The present embodiment includes a sampling system that uses a sampling device 16 which is moved through the field of view of the light measuring device 18. Another embodiment of the present invention uses a fixed sampling device 16 through which the grain sample flows past the quartz window. The speed at which the grain flows within the cell is controlled by adjusting the door between weighing cell and the sampling device. Analysis of the passing sample is performed by capturing images in the light measuring device 18 at a pace that allows for a complete or partial image of the passing grain.

The following examples are illustrative only. It is not intended that the present invention be limited to the illustrative embodiments.

EXAMPLE 1

A bulk corn calibration model is developed according to the following. A group of ninety-six bulk corn samples is selected on the basis of their range of chemical constituents. The samples are derived from five different oil sources and one protein source. The sample set includes foundation lines, $F_1$ lines, inbred lines, and doubled haploid lines. Sample weights ranged from 13 grams to 100 grams. Oil ranges spanned from 4–13% (dry matter basis, DMB), protein from 9–24% (DMB), starch from 60–75% (DMB), and moisture from 9–14%.

The Tecator Infratec 1221 Grain Analyzer (Fos Tecator, P.O. Box 70, S-26321 Hoeganaes, Sweden) is used to obtain reference analysis data along with a commercial calibration model for maize supplied by the manufacturer. The Tecator 1221 Grain Analyzer is a near-infrared diffuse transmittance instrument. It has a built in computer and uses a Partial Least Squares regression based upon Infrasoft Win-ISI software for the development of the calibration equations. The instrument scans between 850–1050 nanometers. A sample cell is used with metal inserts, thereby reducing the active sampling area from 42.8 $cm^2$ to 15.2 $cm^2$. The sample cell has a path length of 2.60 cm. Data acquisition time is 60 seconds per sample not including the time to insert and remove the sample cuvette from the sample compartment.

Figure 11:
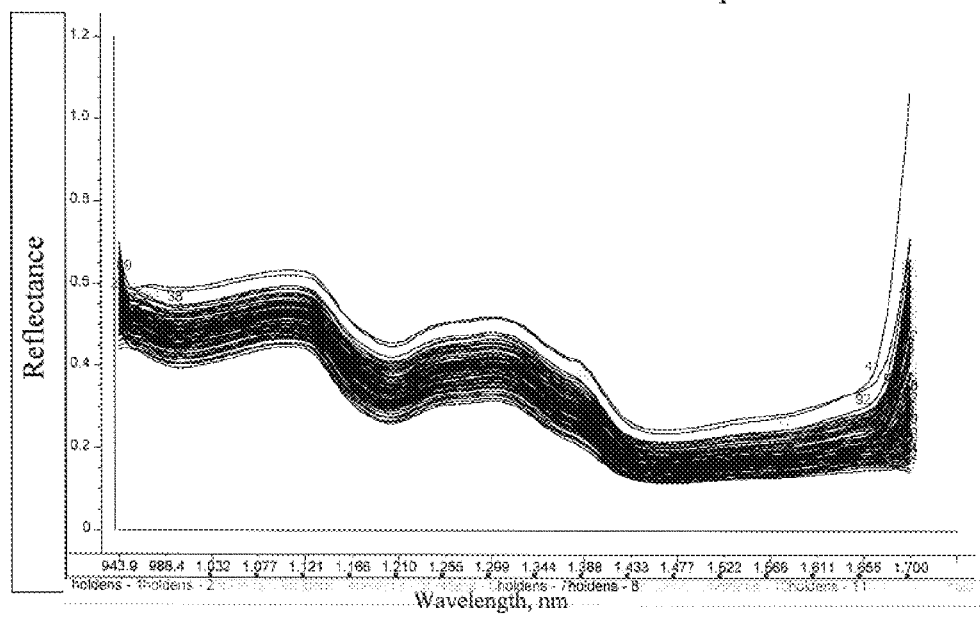
FIG. 11 is a plot of reflectance versus wavelength for averaged spectra of 96 bulk corn samples.
Figure 12:
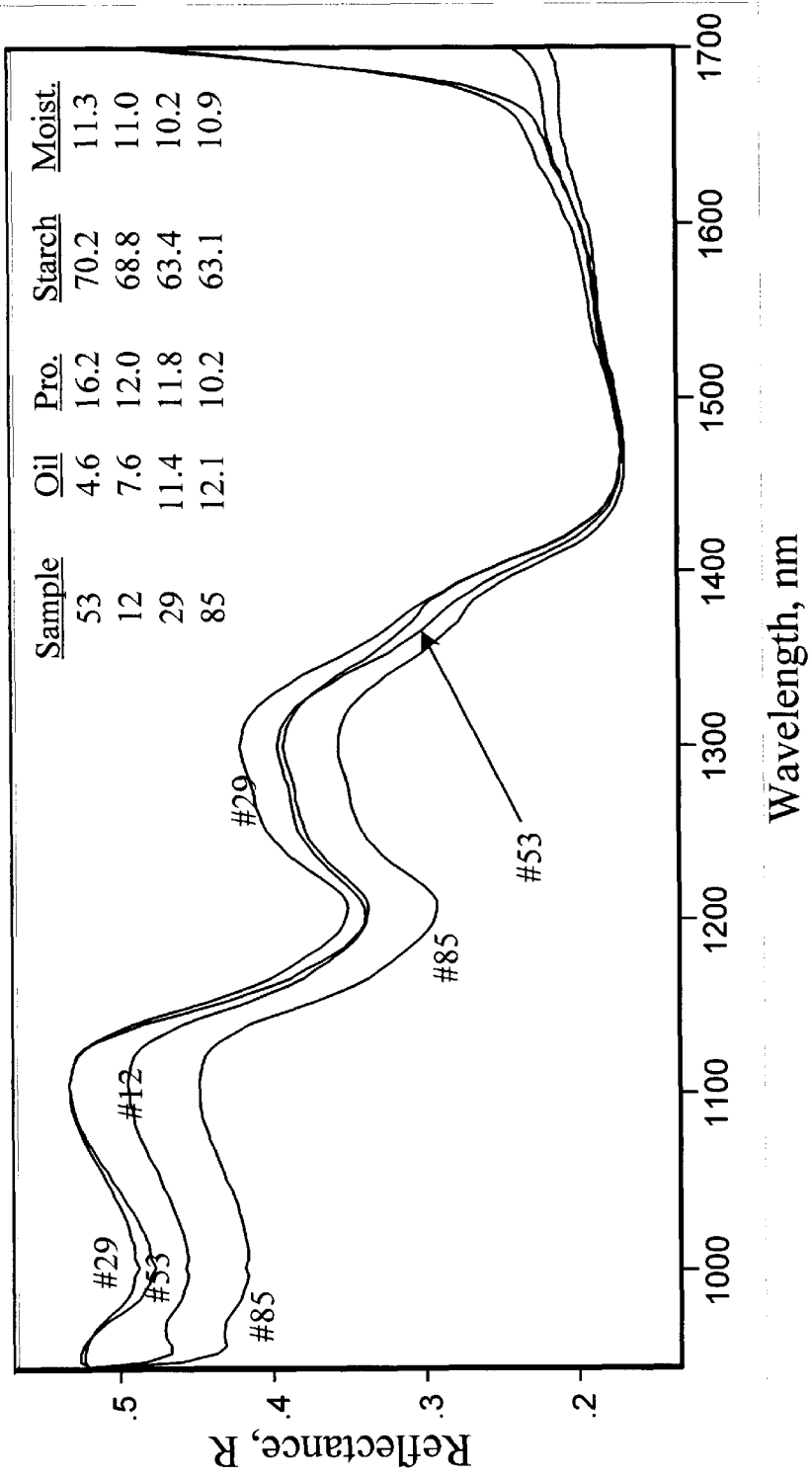
FIG. 12 is a plot of reflectance versus wavelength for four of the averaged spectra shown in FIG. 11.

Samples are run on the device of the present invention using the methods of the present invention as described above. An averaged spectrum is produced for 96 bulk samples by identifying all spatial pixels in a hyper-spectral data cube associated with each sample and averaging the corresponding spectra. A plot of the reflectance versus wavelength for all 96 averaged spectra overlaid is shown in FIG. 11. Representative averaged spectra for four of the 96 bulk corn samples with varying chemical composition is shown in FIG. 12.

Before modeling is performed, each reflectance spectrum is transformed using the Savitsky-Golay second derivative algorithm with a nine point finite difference window and second order polynomial coefficients. Once the spectra are decomposed into their is principle components and weighted by the dependent variables of protein, oil, starch, and moisture, a regression procedure in a partial least squares model is performed on the scores of each spectrum.

Figure 13:
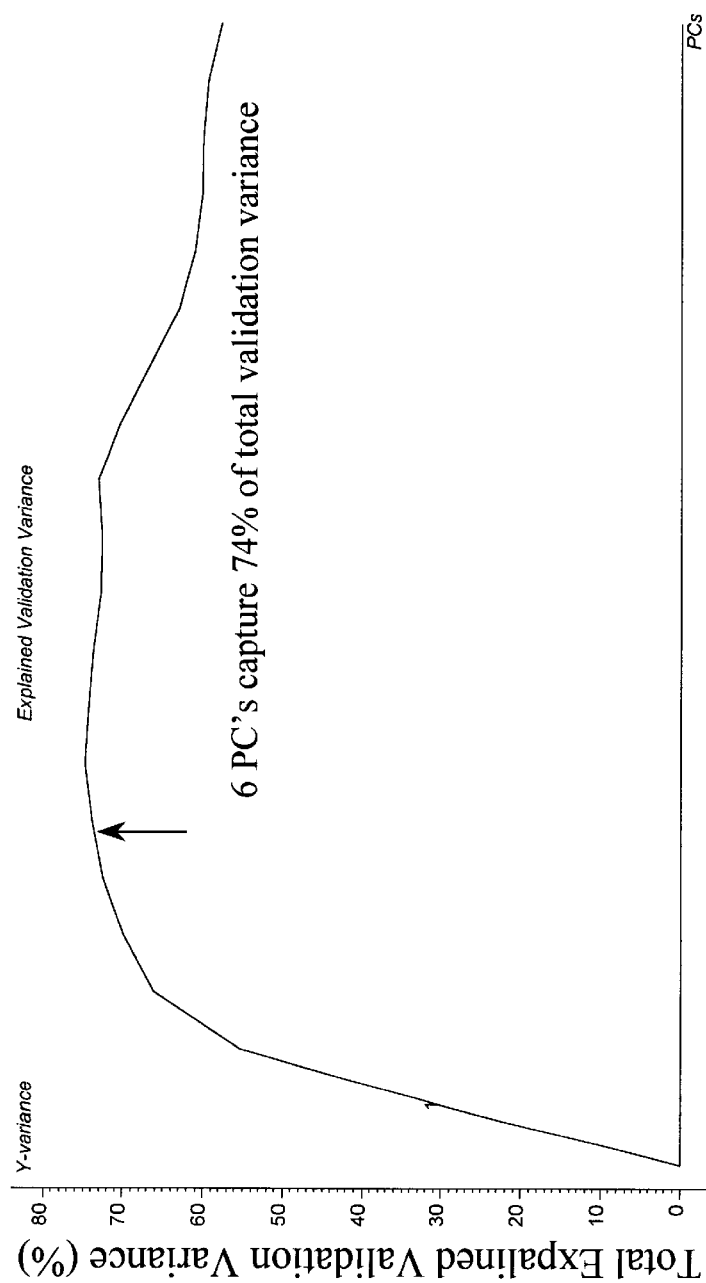
FIG. 13 is a plot of total explained validation variance (%) versus principle component number for bulk corn samples.
Figure 14:
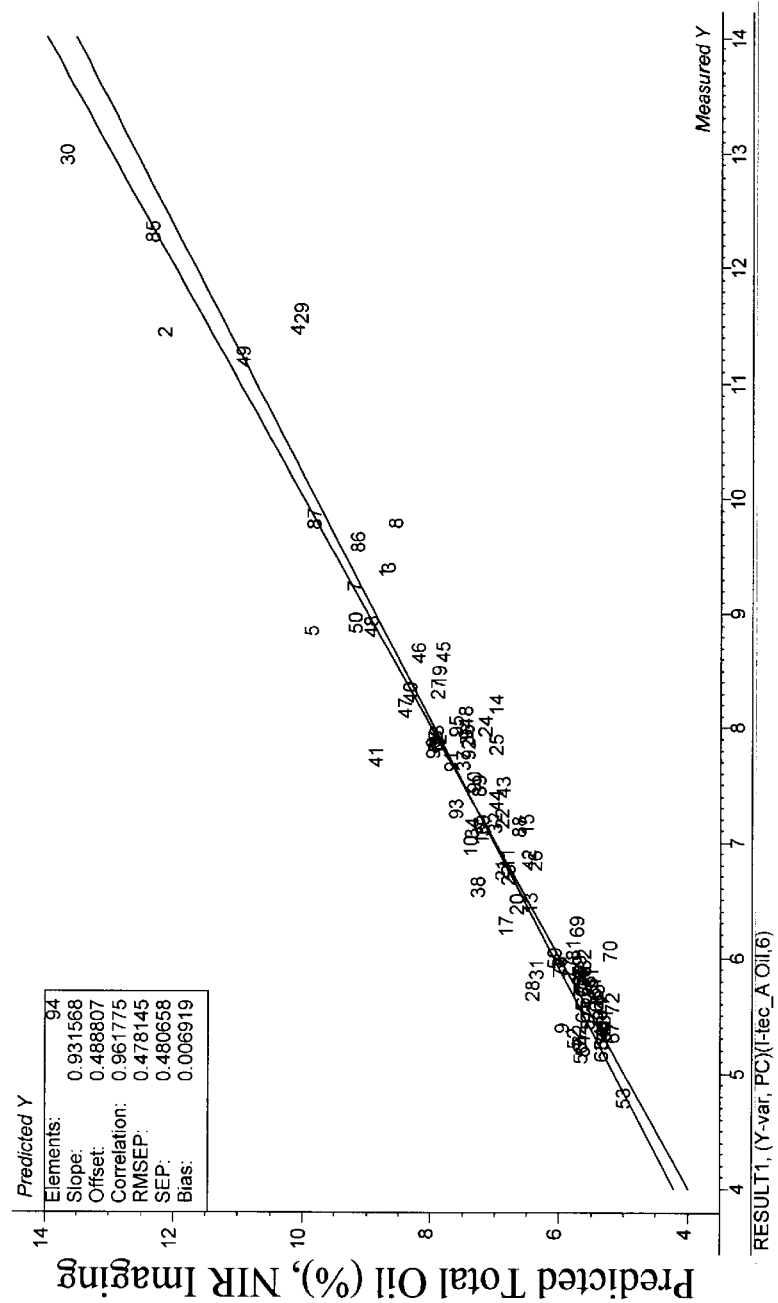
FIG. 14 is a plot of predicted oil content versus reference oil content for bulk corn samples.
Figure 15:
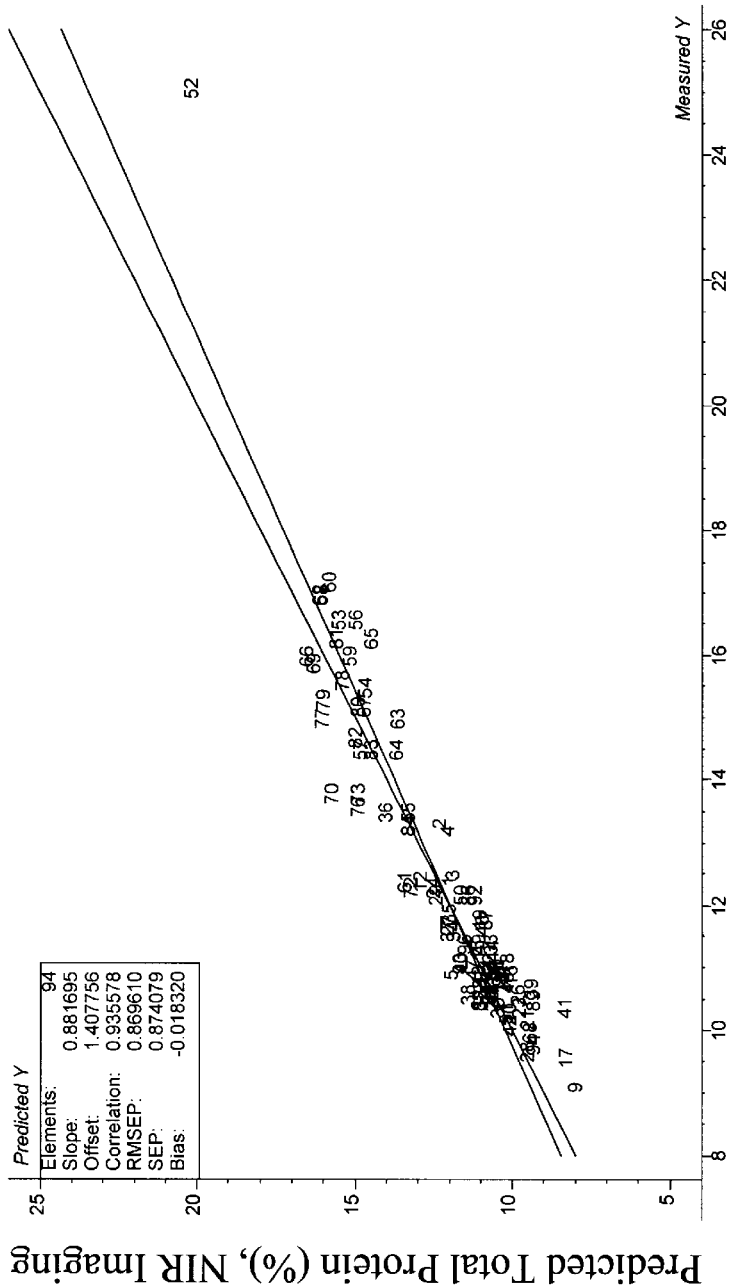
FIG. 15 is a plot of predicted protein content versus reference protein content for bulk corn samples.
Figure 16:
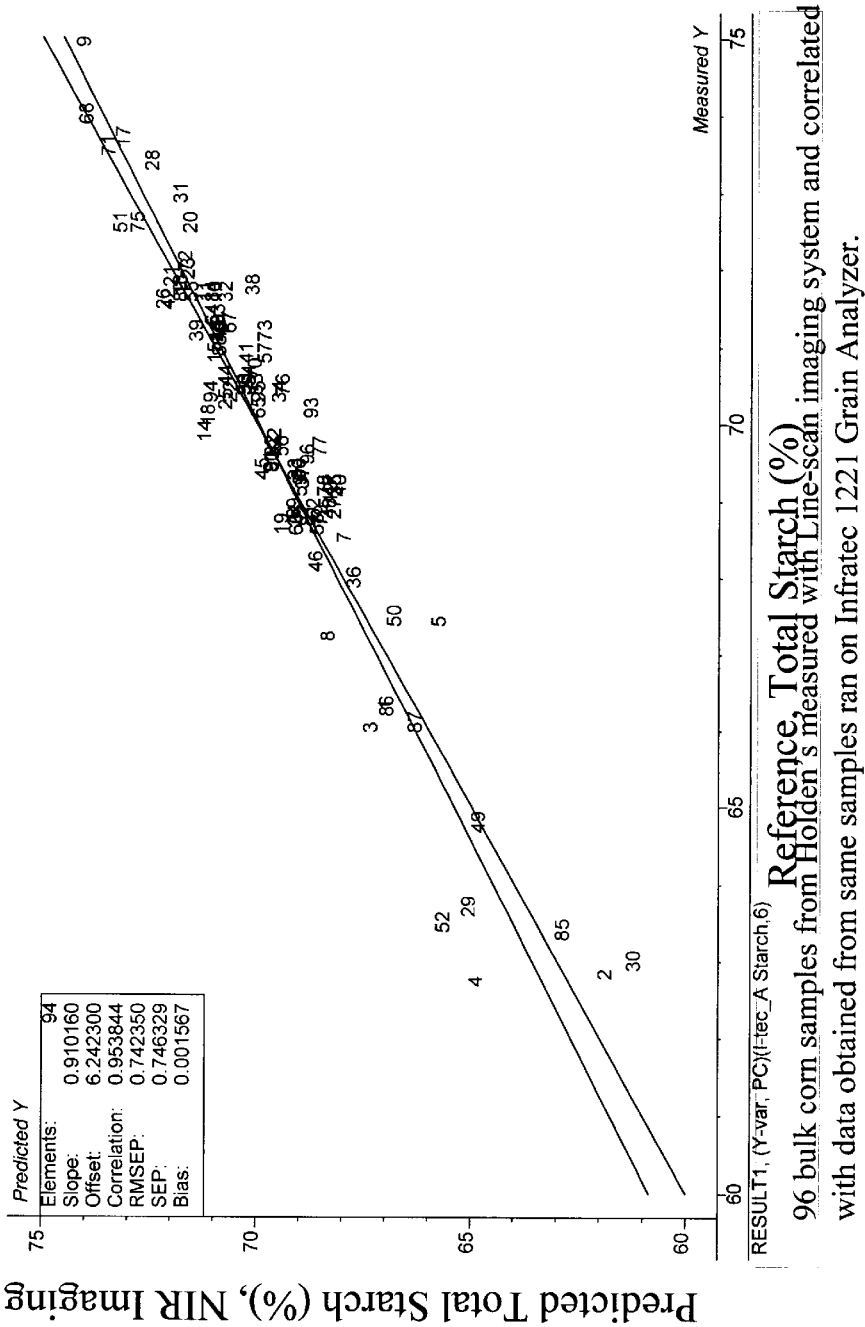
FIG. 16 is a plot of predicted starch content versus reference starch content for bulk corn samples.
Figure 17:
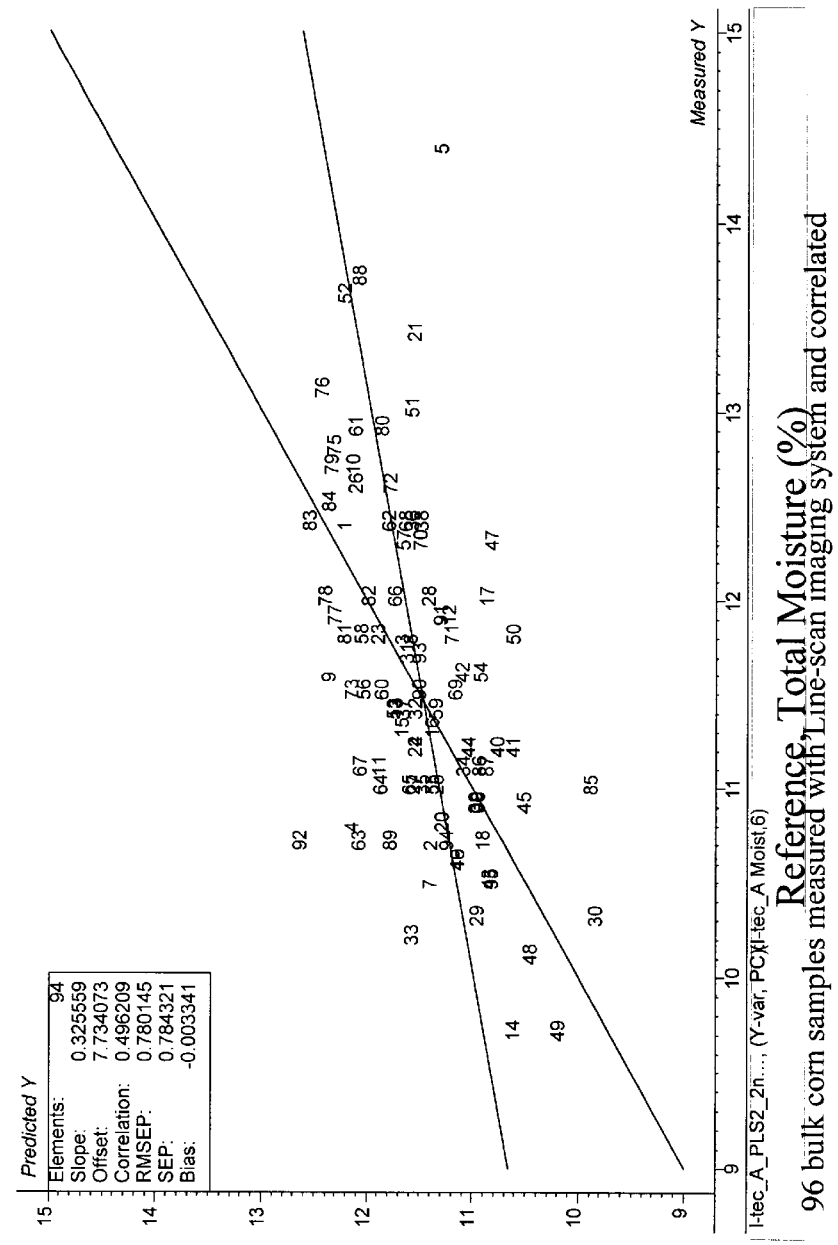
FIG. 17 is a plot of predicted moisture content versus reference moisture content for bulk corn samples.

Modeling is performed on the mean-centered reflectance spectra processed. A single partial least squares (PLS) type-2 model is used for all chemical components of interest: protein, oil, starch, and moisture. Chemometric modeling is performed using The Unscrambler software, (Camo ASA, Oslo, Norway). PLS modeling processes are carried out as described by Haaland and Thomas, *Anal. Chem.*, 60, 1,193–1,202, (1988) and Geladi and Kowalski, *Anal. Chim. Acta*, 185, 1–17, (1986), both of which are herein incorporated by reference in their entirety. Model performance is defined in terms of the multivariate coefficient of determination ($r^2$), the standard error of prediction (SEP) between the measured and modeled values, and the bias between the average value for the measured components and the modeled components. A full cross validation calculation is performed to judge the performance of the model produced. FIG. 13 shows the plot of the total explained validation variance for the Partial Least Squares type 2 model for total oil, protein, starch and moisture for bulk corn versus the principle component number. As can be seen from the plot of FIG. 13, the model captures 74% of the validation variance.

The results of the modeling process are shown in FIGS. 14–17 for oil, protein, starch, and moisture respectively. FIGS. 14–17 are plots of predicted percentages of each trait versus the percentage of the trait as determined by the reference technique. A summary of the performance of the PLS model used is shown in FIG. 18.

EXAMPLE 2

A group of 288 individual corn kernel samples are selected on the basis of their range in chemical constituents. The sample set includes $F_1$ lines, inbred lines, and doubled haploid lines. Sample weight ranges from 100 milligrams to 584 milligrams. Oil ranges spanned from 0.4% to 19.3% (as is basis, not corrected for moisture) as measured on a 23 megahertz Maran NMR single seed spectrometer (Resonance Research Inc., Oxford, England), and protein ranged from 7% to 17% (dry matter basis) as estimated from bulk corn measurements using an Infratec 1221 Near Infrared spectrometer (Fos Tecator, P.O. Box 70, S-26321 Hoeganaes, Sweden).

Figure 19:
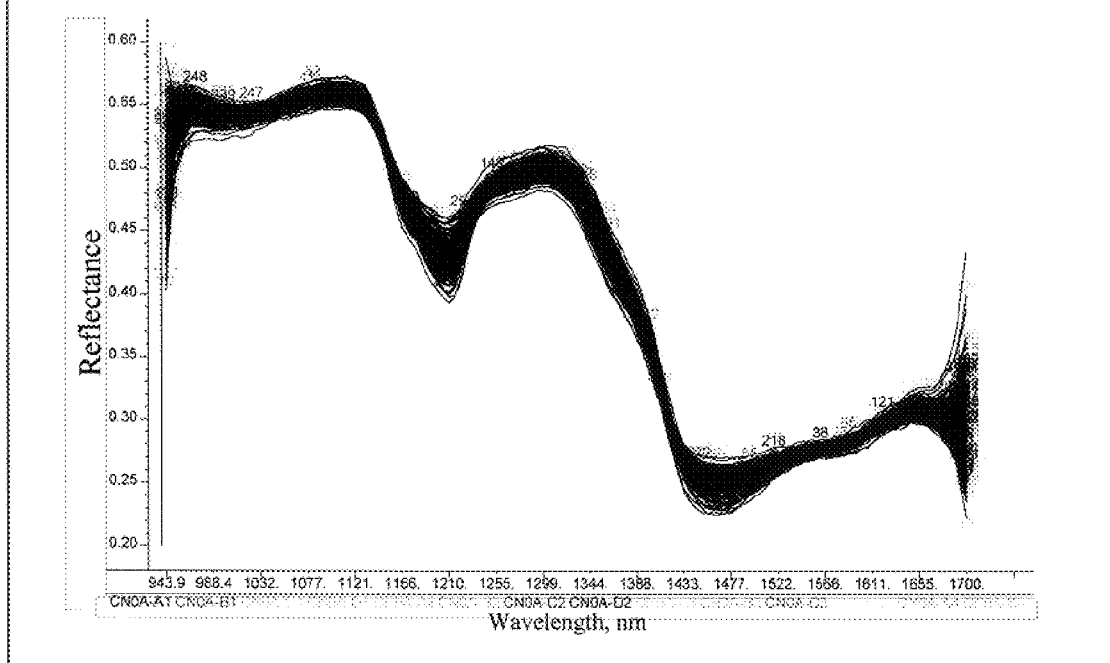
FIG. 19 is a plot of reflectance versus wavelength for 288 single kernel corn samples.
Figure 20:
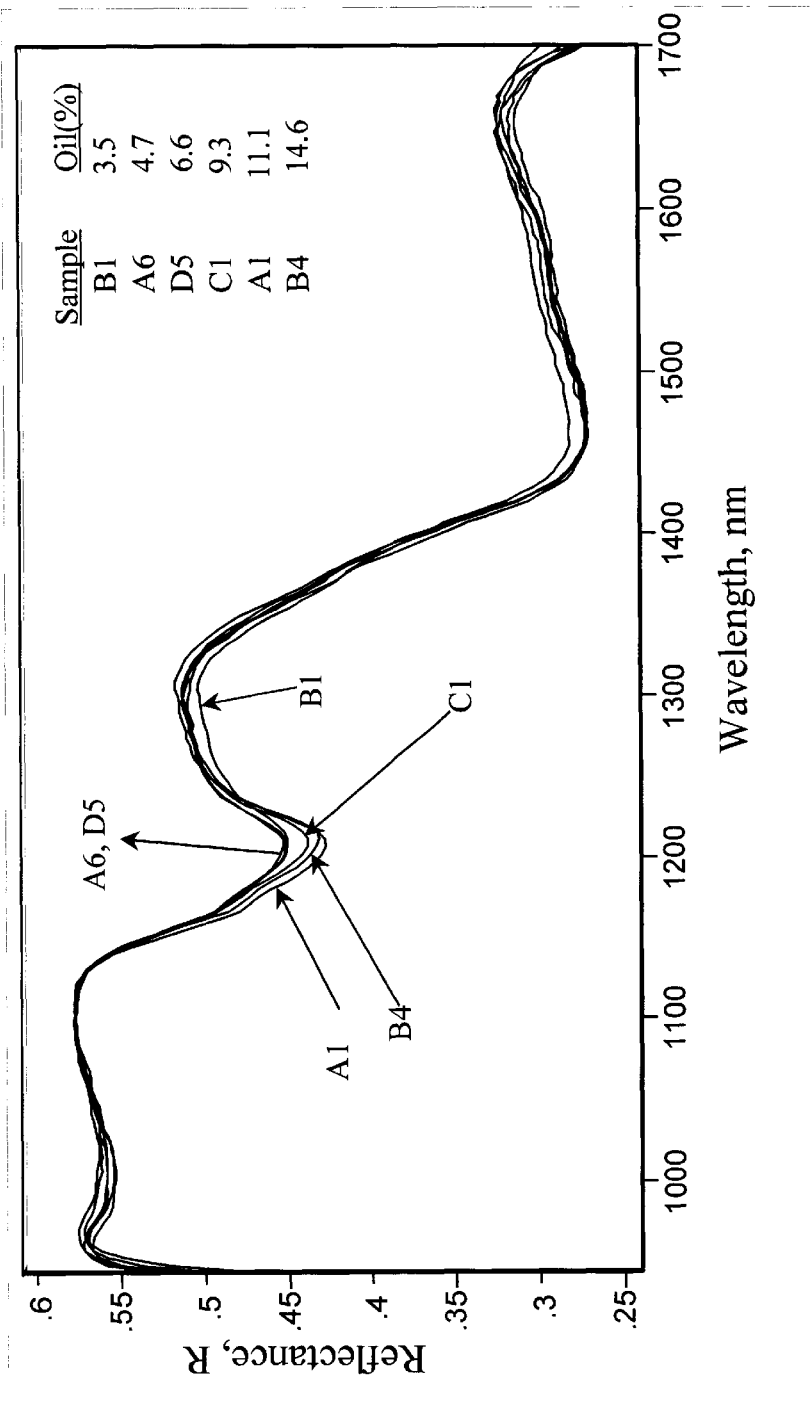
FIG. 20 is a plot of reflectance versus wavelength for 6 representative single kernel corn samples of the samples shown in FIG. 19.

A low field NMR technique was used to determine the absolute concentration of oil for each individual seed. The procedure is non-destructive and does not harm the corn seeds. A Maran Ultra-20 Benchtop NMR spectrometer (Resonance Research Inc., Oxford, England) with an 18 millimeter probe is used to measure the oil for each of the seeds, and the resulting data is used to build the chemometric calibration model. The oil data derived from the spectrometer is not corrected for moisture. The method has a typical analytical range of 0–0.22 grams per seed (0–25% for a 0.22 gram seed), with a typical absolute standard error range of 0.39–0.44%. Sample acquisition time is about 20 seconds per seed. The technique requires an accurate weight for each seed in order to calculate the percent oil concentration A partial least squares (PLS) type-1 model is developed for the chemical component of oil. Chemometric modeling is performed using a commercial software package called The Unscrambler, (Camo ASA, Oslo, Norway). Mathematics of the PLS modeling process are as described for Example 1. An averaged spectrum is produced for each single seed sample by identifying all spatial pixels in the hyper-spectral data cube associated with each seed and averaging the corresponding spectra. A plot of all resulting 288 averaged spectra overlaid is shown in FIG. 19, which is a plot of reflectance versus wavelength. Representative averaged spectra for six single kernel corn samples with varying concentrations of oil are shown in FIG. 20.

Figure 21:
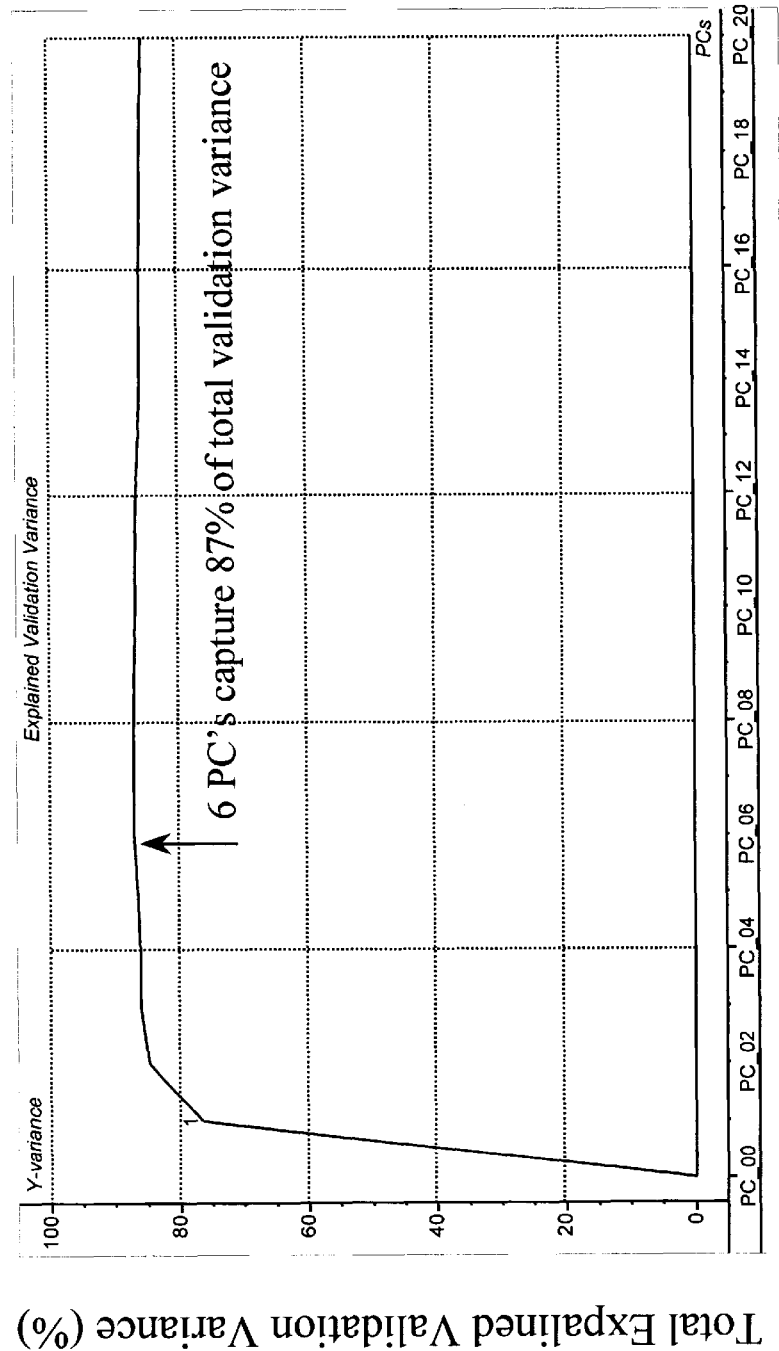
FIG. 21 is a plot of total explained validation variance (%) versus principle component number, single kernel corn.

Before the PLS model calculation is performed, each reflectance spectrum is transformed using a full multiplicative scatter correction (MSC), (see, Martens and Naes, *Near Infrared Technology in Agricultural and Food Industries*, eds., Williams and Norris, Am. Assoc. Cereal Chem.) and using the Savitsky-Golay second derivative algorithm with a 15 point finite difference window and second order polynomial coefficients. Modeling is performed on the mean-centered reflectance spectra as in Example 1. The regression procedure in a PLS model is performed on the scores of each spectrum, once the spectra are decomposed into their principle components and weighted by the dependent variable of oil. Model performance is defined in terms of the multivariate coefficient of determination ($r^2$), the standard error of prediction (SEP) between the measured and modeled values, and the bias between the average value for the measured components and the modeled components. A full cross validation calculation is performed to judge the performance of the model produced. FIG. 21 shows the plot of the total explained validation variance for the PLS type 1 model for total oil for single kernel corn versus the principle component number. As can be seen from the plot in FIG. 21, the model captures 87% of the total validation variance.

Figure 22:
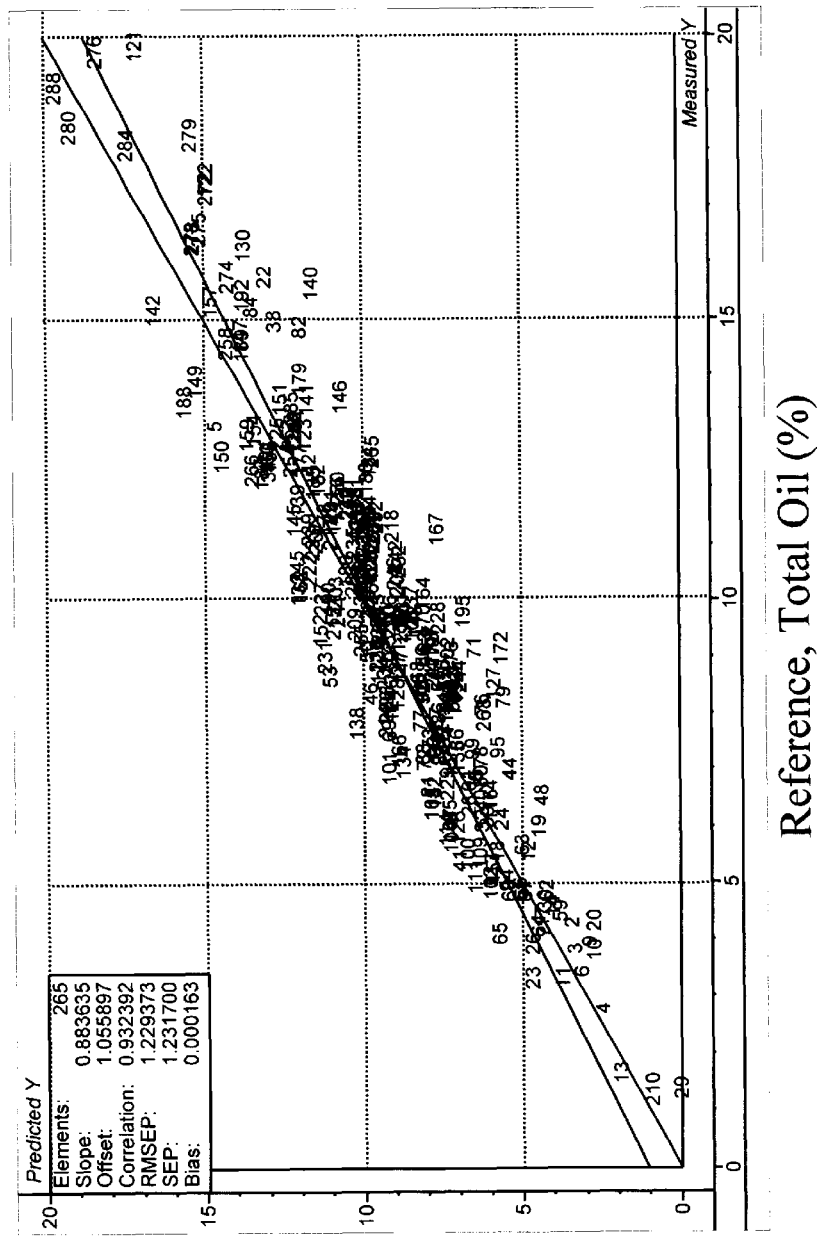
FIG. 22 is a plot of predicted oil percentage versus reference oil percentage for 265 single kernel samples.

The results of the modeling process for oil are shown in FIG. 22. For this PLS model developed for total oil with 265 calibration samples, the muiltivariate coefficient of determination, $r^2$, was 0.93, with a standard error of prediction, SEP, of 1.23, and a bias between the average value for the measured values and the modeled predicted values was 0.000163.

What is claimed is:

1. A method for determining whether a seed exhibits a trait, comprising the steps of:
   (A) receiving said seed;
   (B) directing light from a light source to said seed, thereby forming emitted light;
   (C) dispersing said emitted light to form dispersed light;
   (D) receiving said dispersed light in a light measuring device comprising an array of multiple datapoints, the array including a spatial dimension defining multiple sample points on the seed and a spectral dimension defining spectral data for the dispersed light from each of the multiple sample points;
   (E) outputting a spectral data signal for each of said multiple datapoints with said light measuring device; and,
   (F) determining whether said seed exhibits said trait at individual ones of the multiple sample points based on said spectral data signals.

2. A method according to claim 1, wherein said trait is a quantitative trait.

3. A method according to claim 1, wherein said trait is a biochemical trait.

4. A method according to claim 3, wherein said biochemical trait is selected from the group consisting of oil content, protein content, carbohydrate content, starch content, fiber content and water content.

5. A method according to claim 3, wherein said biochemical trait is selected from the group consisting of oil composition, protein composition, carbohydrate composition, and fiber composition.

6. A method according to claim 1, wherein said trait is a morphological trait.

7. A method according to claim 6, wherein said morphological trait is selected from endosperm size, germ size, seed shape, seed size, seed color, seed surface texture, seed weight, seed density, and seed integrity.

8. A method according to claim 1, wherein the emitted light is selected from the group consisting of reflected light from the seed at each of the multiple sample points and transmitted light passed through the seed at each of the multiple sample points.

9. A method according to claim 7, wherein said seed integrity is correlated to disease susceptibility or resistance.

10. A method according to claim 7, wherein said seed integrity is correlated to resistance or susceptibility to insect infestation.

11. A method according to claim 7, wherein said seed integrity is correlated to resistance or susceptibility to fungal infestation.

12. A method according to claim 7, wherein said seed integrity is whole seed integrity.

13. A method according to claim 1, wherein said dispersed light is between the wavelengths of 900 and 1,700 nm.

14. A method according to claim 1, wherein said dispersed light provides a spectral image at least in the 900 to 1,700 nm spectral range, a spectral dispersion of at least 150 nm/mm and at least a 20 nm spectral resolution.

15. A method according to claim 1, wherein said light source is capable of providing light comprising wavelengths in the range 900 to 1,700 nanometers.

16. A method according to claim 1, wherein steps (A) to (F) can be performed in less than 5 seconds.

17. A method according to claim 1, wherein in step (F) it is determined if more than one trait is exhibited.

18. A method according to claim 1, wherein said trait is quantity of oil in endosperm.

19. A method according to claim 1, wherein said step of determining comprises the step of determining a relative spatial distribution of the trait within the seed.

20. A method for determining whether a plant tissue exhibits a trait comprising the steps of:
 (A) receiving said plant tissue;
 (B) directing light from a light source to said plant tissue, thereby forming transmitted or reflected light;
 (C) dispersing said transmitted or reflected light to form dispersed light;
 (D) receiving said dispersed light in a light measuring device comprising an array of multiple datapoints, the array including a spatial dimension defining multiple sample points on the plant tissue and a spectral dimension defining spectral data for the dispersed light from each of the multiple sample points;
 (E) outputting a spectral data signal for each of said multiple datapoints with said light measuring device; and,
 (F) determining whether plant tissue exhibits said trait at individual ones of the multiple sample points based on said spectral data signals.

21. A method for determining whether a batch of seeds contains seeds which exhibit a trait comprising:
 (A) receiving said batch of seeds;
 (B) directing light from a light source to said batch of seeds, thereby forming transmitted or reflected light;
 (C) dispersing said transmitted or reflected light to form dispersed light;
 (D) receiving said dispersed light in a light measuring device comprising an array of multiple datapoints, the array including a spatial dimension defining multiple sample points on the batch of seeds and a spectral dimension defining spectral data for the dispersed light from each of the multiple sample points;
 (E) outputting a spectral data signal for each of said multiple datapoints with said light measuring device; and,
 (F) determining whether individual seeds in said batch of seeds exhibit said trait based on said spectral data signals, wherein said step of determining comprises the step of associating said individual seeds with corresponding ones of the multiple sample points.

22. The method of claim 21, wherein said step of receiving said batch of seeds comprises the step of providing an individual compartment within a sampling device for each of said seeds in said batch of seeds, thereby allowing individual sorting of seeds after said determining whether individual seeds of said batch of seed exhibit said trait.

23. The method as in claim 21, wherein said batch of seeds comprises more than 10 individual seeds.

24. The method as in claim 21, wherein the step of dispersing comprises the step of dispersing said transmitted or reflected light to form dispersed light corresponding to multiple sample points in each individual seed across the batch of seeds, and wherein the step of determining comprises the step of determining whether the individual seed exhibits said trait at individual ones of the multiple sample points based on said spectral data signals.

25. The method as in claim 21, wherein said batch of seeds comprises more than 50 individual seeds.

26. The method as in claim 21, wherein said method can be performed on said batch of seeds in less than about 10 seconds.

27. The method as in claim 21, wherein said method can be performed on said batch of seeds in less than about 5 seconds.

28. A method for determining whether a sample exhibits a trait, comprising the steps of:
 directing light on the sample to produce light of mixed wavelengths emitted at a plurality of discrete spatial sample points from the sample;
 dispersing the emitted light of mixed wavelengths for each discrete spatial sample points into a corresponding spectral image comprising a plurality of component wavelengths;
 detecting, with respect to each discrete spatial sample point, component wavelengths within the corresponding spectral image; and
 processing the detected component wavelengths against a model to determine whether the sample exhibits a certain trait at each of the discrete spatial sample points, the model associating the existence of certain component wavelengths in the spectral image with the presence of the exhibited certain trait at the corresponding discrete spatial sample point for the sample.

29. The method of claim 28 wherein the sample is an agricultural product comprising one of an individual seed, a batch of seeds and a plant tissue.

30. The method of claim 28 wherein the emitted light comprises reflected light from the sample.

31. The method of claim 28 wherein the emitted light comprises transmitted light passed through the sample.

32. The method of claim 28 wherein the step of processing further comprises the step of determining a quantitative amount of the exhibited certain trait at each of the discrete spatial sample points.

33. The method of claim 28 wherein the trait comprises a biochemical trait selected from the group consisting of oil, protein, carbohydrate, starch, fiber and water.

34. The method of claim 33 wherein the biochemical trait of starch further comprises a starch phenotype selected from the group consisting of amylopectin and amylose.

35. The method of claim 28 wherein the trait comprises endosperm mutation characteristics selected from the group consisting of reduced zeins in the endosperm and amino acid quantities.

36. The method of claim 28 wherein the trait comprises a morphological trait selected from the group consisting of endosperm size, germ size, seed shape seed color, seed surface texture, seed weight, seed density and seed integrity.

37. The method of claim 28 wherein the trait comprises an indicator of kernel breakage selected from the group consisting of the ratio of vitreous to non-vitreous endosperm, kernel density, average kernel weight, pericarp quantity, pericarp quality, kernel size and kernel shape.

38. The method of claim 28 wherein the step of directing light comprises the step of directing light comprising wavelengths in range of 900 to 1,700 nanometers.

39. The method of claim 28 wherein the step of dispersing comprises the step of dispersing the emitted light into the spectral image having a spectral dispersion of at least 150 nm/mm and at least a 20 nm spectral resolution.

40. The method of claim 28 further including the step of:
measuring the weight of the sample; and
wherein the step of processing further includes the step of determining a quantitative amount of the exhibited certain trait per measured weight of the sample.

41. The method of claim 28 further including step of sorting the sample among a plurality of destinations based on the determined presence of the exhibited certain trait.

42. The method of claim 28 further including the step of selecting preferred individuals of the sample based on the determined presence of the exhibited certain trait.

43. Apparatus for determining whether a sample exhibits a trait, comprising:
a light source directing light on the sample to produce light of mixed wavelengths emitted at a plurality of discrete spatial sample points from the sample;
a spectrograph that disperses the emitted light of mixed wavelengths for each discrete spatial sample point into a corresponding spectral image comprising a plurality of component wavelengths;
a camera including a detector for detecting, with respect to each discrete spatial sample point, component wavelengths within the corresponding spectral image; and
a processor operable to compare the detected component wavelengths against a model to determine whether the sample exhibits a certain trait at each of the discrete spatial sample points, the model associating the existence of certain component wavelengths in the spectral image with the presence of the exhibited certain trait at the corresponding discrete spatial sample point for the sample.

44. The apparatus of claim 43 wherein the sample is an agricultural product comprising one of an individual seed, a batch of seeds and a plant tissue.

45. The apparatus of claim 43 wherein the emitted light comprises reflected light from the sample.

46. The apparatus of claim 43 wherein the emitted light comprises transmitted light passed through the sample.

47. The apparatus of claim 43 wherein the processor further operates to determine a quantitative amount of the exhibited certain trait at the discrete sample points.

48. The apparatus of claim 43 wherein the trait comprises a biochemical trait selected from the group consisting of oil, protein, carbohydrate, starch, fiber and water.

49. The apparatus of claim 43 wherein the biochemical trait of starch further comprises a starch phenotype selected from the group consisting of amylopectin and amylose.

50. The apparatus of claim 43 wherein the trait comprises endosperm mutation characteristics selected from the group consisting of reduced zeins in the endosperm and amino acid quantities.

51. The apparatus of claim 43 wherein the trait comprises a morphological trait selected from the group consisting of endosperm size, germ size, seed shape seed color, seed surface texture, seed weight, seed density and seed integrity.

52. The apparatus of claim 43 wherein the trait comprises an indicator of kernel breakage selected from the group consisting of the ratio of vitreous to non-vitreous endosperm, kernel density, average kernel weight, pericarp quantity, pericarp quality, kernel size and kernel shape.

53. The apparatus of claim 43 wherein the light source directs light comprising wavelengths in range of 900 to 1,700 nanometers.

54. The apparatus of claim 43 wherein the spectrograph disperses the emitted light into the spectral image having a spectral dispersion of at least 150 nm/mm and at least a 20 nm spectral resolution.

55. The apparatus of claim 43 further including:
a device for measuring the weight of the sample; and
wherein the processor further operates to determine a quantitative amount of the exhibited certain trait per measured weight of the sample.

56. The apparatus of claim 43 further including a sorter operable to receive the sample and sort the sample among a plurality of destinations based on the processor determined presence of the exhibited certain trait.

57. The apparatus of claim 43 further including:
a sample holder for holding the sample; and
a linear translation stage supporting the sample holder and operable to move the sample holder relative to the spectrograph to effectuate a scanning of light from the light source across, and the production of mixed wavelength lights emitted at a plurality of discrete spatial sample points over, the sample held therein.

58. The apparatus of claim 57 wherein the light from the light source is formed into a light line that is scanned by linear translation stage movement of the sample holder across the sample.

59. The apparatus of claim 43 further comprising a processing device selected from the group consisting of a sheller, thresher and combine for providing the sample for trait determination analysis.

60. The apparatus according to claim 43, wherein said spectrograph is selected from the group consisting of a prism-grating-prism spectrograph or a reflective grating spectrograph.

61. The apparatus according to claim 43, wherein said light source is selected from the group consisting of halogen, tungsten halogen, long filament halogen, xenon, xenon flash, fluorescent, neon, and mercury.

62. The apparatus according to claim 43, wherein said camera is selected from the group consisting of an Indium Antimonide camera, a Mercury Cadmium Telluride camera, a Platinum Silicide camera, an Arsenic-doped Silicon camera, an Indium Gallium Arsenide camera, and a CCD camera.

63. A method, comprising the steps of
(A) directing a line of light on a portion of an agricultural sample to produce emitted light;
(B) dispersing the emitted light into a corresponding spectral image comprising a plurality of component wavelengths for each of a plurality of discrete spatial sample points on portion of the agricultural sample along the line of light;
(C) detecting, with respect to each discrete spatial sample point along the line of light, component wavelengths within the corresponding spectral image;
(D) repeating steps (A)–(C) to scan each portion of the agricultural sample; and
(E) producing from the detected component wavelengths at each discrete spatial sample point for each of the scanned portions a hyperspectral datacube for the agricultural sample.

64. The method as in claim 63 further including the step of processing the detected component wavelengths in the hyperspectral datacube against a model to determine whether the agricultural sample exhibits a certain trait at each of the discrete spatial sample points, the model associating the existence of certain component wavelengths in the spectral image with the presence of the exhibited certain trait at the corresponding discrete spatial sample point for the agricultural sample.

65. The method as in claim 63 further including the step of processing the detected component wavelengths in the hyperspectral datacube associated with discrete spatial sample points in a certain portion against a model to determine whether the agricultural sample exhibits a certain trait at each of the discrete spatial sample points in that certain portion, the model associating the existence of certain component wavelengths in the spectral image with the presence of the exhibited certain trait at the corresponding discrete spatial sample points of the certain portion for the agricultural sample.

66. The method as in claim 63 further including the step of processing the detected component wavelengths in the hyperspectral datacube associated with discrete spatial sample points in a certain portion against a model to determine whether the agricultural sample exhibits a certain trait at the certain portion, the model associating the existence of certain component wavelengths in the spectral images for the discrete spatial sample points in the certain portion with the presence of the exhibited certain trait at the certain portion of the agricultural sample.

67. The method as in claim 66 further including the step of averaging the detected component wavelengths in the hyperspectral datacube associated with discrete spatial sample points in a certain portion to form an average spectrum for the certain portion for processing against the model.

68. An apparatus, comprising the steps of:
- a light source directing a line of light on a portion of the agricultural sample to produce emitted light,
- a spectrograph dispersing the emitted light into a corresponding spectral image comprising a plurality of component wavelengths for each of a plurality of discrete spatial sample points on the portion of the agricultural sample along the line of light;
- a camera including a detector for detecting, with respect to each discrete spatial sample point, component wavelengths within the corresponding spectral image;
- means for moving the agricultural sample relative to the line of light to scan each portion of the agricultural sample; and
- a processor operable to produce from the detected component wavelengths at each discrete spatial sample point for each of the scanned portions a hyperspectral datacube for the agricultural sample.

69. The apparatus of claim 68 wherein the agricultural sample is selected from the group consisting of a seed, a batch of seeds, and a plant tissue.

70. The apparatus of claim 68 wherein the means for moving comprises:
- a sample holder for holding the agricultural sample; and
- a linear translation stage supporting the sample holder and operable to move the sample holder relative to the line of light.

71. The apparatus as in claim 68 wherein the processor is further operable to process the detected component wavelengths in the hyperspectral datacube against a model to determine whether the agricultural sample exhibits a certain trait at each of the discrete spatial sample points, the model associating the existence of certain component wavelengths in the spectral image with the presence of the exhibited certain trait at the corresponding discrete spatial sample point for the agricultural sample.

72. The apparatus as in claim 68 wherein the processor is further operable to process the detected component wavelengths in the hyperspectral datacube associated with discrete spatial sample points in a certain portion against a model to determine whether the agricultural sample exhibits a certain trait at each of the discrete spatial sample points in that certain portion, the model associating the existence of certain component wavelengths in the spectral image with the presence of the exhibited certain trait at the corresponding discrete spatial sample points of the certain portion for the agricultural sample.

73. The apparatus as in claim 68 wherein the processor is further operable to process the detected component wavelengths in the hyperspectral datacube associated with discrete spatial sample points in a certain portion against a model to determine whether the agricultural sample exhibits a certain trait at the certain portion, the model associating the existence of certain component wavelengths in the spectral images for the discrete spatial sample points in the certain portion with the presence of the exhibited certain trait at the certain portion of the agricultural sample.

74. The apparatus as in claim 73 wherein the processor is further operable to average the detected component wavelengths in the hyperspectral datacube associated with discrete spatial sample points in a certain portion to form an average spectrum for the certain portion for processing against the model.

75. A method for introgressing a trait into a plant, comprising the steps of
- (A) directing light from a light source to a seed, thereby forming emitted light;
- (B) dispersing said emitted light to form dispersed light;
- (C) receiving said dispersed light in a light measuring device comprising an array of multiple datapoints, the array including a spatial dimension defining multiple sample points on the seed and a spectral dimension defining spectral data for the dispersed light from each of the multiple sample points;
- (D) outputting a spectral data signal for each of said multiple datapoints with said light measuring device;
- (E) determining whether said seed exhibits a trait of interest at individual ones of the multiple sample points based on said spectral data signals;
- (F) selecting the seed for breeding if the step of determining identifies the seed as exhibits the trait of interest;
- (G) growing a fertile plant from the selected seed; and
- (H) using the fertile plant as a parent plant in a cross with another plant.

76. The method as in claim 75 wherein the cross results in a progeny plant which produces seed and further including the step of selecting seed of that progeny plant using steps (A)–(F).

77. The method as in claim 75 wherein the fertile plant is a male parent to said cross.

78. The method as in claim 75 wherein the fertile plant is a female parent to said cross.

79. The method of claim 75 wherein the cross results in a progeny plant which produces seed and further including the step of repeating steps (A)–(H) to selectively breed plants whose seeds have the trait of interest.

80. Apparatus for determining whether a seed exhibits a trait, comprising:
  a sampling device for holding said seed;
  a light source directing light to said seed, thereby forming emitted light;
  a spectrograph dispersing said emitted light to form dispersed light;
  a light measuring device that receives said dispersed light, the device comprising an array of multiple datapoints, the array including a spatial dimension defining multiple sample points on the seed and a spectral dimension defining spectral data for the dispersed light from each of the multiple sample points, the device outputting a spectral data signal for each of said multiple datapoints; and
  a processor for determining whether said seed exhibits said trait at individual ones of the multiple sample points based on said spectral data signals.

81. The apparatus according to claim 80, wherein said trait is a quantitative trait.

82. The apparatus according to claim 80, wherein said trait is a biochemical trait.

83. The apparatus according to claim 82, wherein said biochemical trait is selected from the group consisting of oil content, protein content, carbohydrate content, starch content, fiber content and water content.

84. The apparatus according to claim 82, wherein said biochemical trait is selected from the group consisting of oil composition, protein composition, carbohydrate composition, and fiber composition.

85. The apparatus according to claim 80, wherein said trait is a morphological trait.

86. The apparatus according to claim 85, wherein said morphological trait is selected from endosperm size, germ size, seed shape, seed size, seed color, seed surface texture, seed weight, seed density, and seed integrity.

87. The apparatus according to claim 85, wherein said seed integrity is correlated to disease susceptibility or resistance.

88. The apparatus according to claim 87, wherein said disease susceptibility or resistance is resistance or susceptibility to insect infestation.

89. The apparatus according to claim 87, wherein said disease susceptibility or resistance is resistance or susceptibility to fungal infestation.

90. The apparatus according to claim 87, wherein said seed integrity is whole seed integrity.

91. The apparatus according to claim 80, wherein the emitted light is selected from the group consisting of reflected light from the seed at each of the multiple sample points and transmitted light passed through the seed at each of the multiple sample points.

92. The apparatus according to claim 80, wherein said dispersed light is between the wavelengths of 900 and 1,700 nm.

93. The apparatus according to claim 80, wherein said spectrograph is capable of providing dispersed light for a spectral image at least in the 900 to 1,700 nm spectral range, a spectral dispersion of at least 150 nm/mm and at least a 20 nm spectral resolution.

94. The apparatus according to claim 80, wherein said spectrograph is selected from the group consisting of a prism-grating-prism spectrograph or a reflective grating spectrograph.

95. The apparatus according to claim 80, wherein said light source is capable of providing light comprising wavelengths in the range 900 to 1,700 nanometers.

96. The apparatus according to claim 80, wherein said light source is selected from the group consisting of halogen, tungsten halogen, long filament halogen, xenon, xenon flash, fluorescent, neon, and mercury.

97. The apparatus according to claim 80, wherein said sampling device is selected from the group consisting of transparent containers comprising a generally horizontal surface.

98. The apparatus according to claim 80, wherein said sampling device is mounted on a linear translational stage capable of moving relative to said spectrometer.

99. The apparatus according to claim 80, wherein said light measuring device comprises a focal plane having greater than 75,000 pixels, less than a 20 micron pitch, and a frame rate in excess of 25 frames per second.

100. The apparatus according to claim 80, wherein said light measuring device is selected from the group consisting of an Indium Antimonide camera, a Mercury Cadmium Telluride camera, a Platinum Silicide camera, an Arsenic-doped Silicon camera, an Indium Gallium Arsenide camera, and a CCD camera.

101. The apparatus according to claim 80, wherein the processor determines whether more than one trait is exhibited.

102. A method for differentiating haploid samples from non-haploid samples, comprising the steps of:
  directing light on a seed to produce light of mixed wavelengths emitted at a plurality of discrete spatial sample points from the seed;
  dispersing the emitted light of mixed wavelengths for each discrete spatial sample point into a corresponding spectral image comprising a plurality of component wavelengths;
  detecting, with respect to each discrete spatial sample point, component wavelengths within the corresponding spectral image; and
  processing the detected component wavelengths for each of the discrete spatial sample points on the seed against a model to determine whether the seed is a haploid, the model associating the existence of certain component wavelengths in the spectral image with a phenotype produced by a haploid trait.

103. The method of claim 102 wherein the emitted light comprises reflected light from the agricultural product.

104. The method of claim 102 wherein the emitted light comprises transmitted light passed through the agricultural product.

105. The method of claim 102 wherein the step of processing further comprises the step of differentiating the location of the endosperm within the seed.

106. The method of claim 105 wherein the step of processing further comprises the step of processing the detected component wavelengths for those discrete spatial sample points within the endosperm of the seed to detect anthocyainin coloration indicative of the seed being a haploid.

107. The method of claim 102 wherein the step of processing further comprises the step of differentiating the location of the embryo within the seed.

108. The method of claim 107 wherein the step of processing further comprises the step of processing the detected component wavelengths for those discrete spatial sample points within the embryo of the seed to detect a lack of coloration indicative of the seed being a haploid.

109. The method of claim 102 further including step of sorting the seed among a plurality of destinations based on whether the seed is determined to be a haploid.

110. The method of claim 102 further including the step of selecting the seed based on a determination that the seed is a haploid.

111. Apparatus for differentiating haploid samples from non-haploid samples, comprising:
- a light source directing light on a seed agricultural product to produce light of mixed wavelengths emitted at a plurality of discrete spatial sample points from the seed;
- a spectrograph that disperses the emitted light of mixed wavelengths for each discrete spatial sample point into a corresponding spectral image comprising a plurality of component wavelengths;
- a camera including a detector for detecting, with respect to each discrete spatial sample point, component wavelengths within the corresponding spectral image; and
- a processor operable to compare the detected component wavelengths for each of the discrete spatial sample points on the seed against a model to determine whether the seed is a haploid, the model associating the existence of certain component wavelengths in the spectral image with a phenotype produced by a haploid trait.

112. The apparatus of claim 111 wherein the emitted light comprises reflected light from the agricultural product.

113. The apparatus of claim 111 wherein the emitted light comprises transmitted light passed through the sample.

114. The apparatus of claim 111 wherein the processor is further operable to differentiate the location of the endosperm within the seed.

115. The apparatus of claim 114 wherein the processor is further operable to process the detected component wavelengths for those discrete spatial sample points within the endosperm of the seed to detect anthocyainin coloration indicative of the seed being a haploid.

116. The apparatus of claim 111 wherein the processor is further operable to differentiate the location of the embryo within the seed.

117. The apparatus of claim 116 wherein the processor is further operable to process the detected component wavelengths for those discrete spatial sample points within the embryo of the seed to detect a lack of coloration indicative of the seed being a haploid.

118. The apparatus of claim 111 further including a sorter that directs the seed among a plurality of destinations based on whether the seed is determined to be a haploid.

119. The apparatus of claim 111 further including a selector for choosing the seed based on a determination that the seed is a haploid.

120. A method for differentially analyzing portions of an agricultural sample, comprising the steps of:
- directing light on an agricultural sample to produce light of mixed wavelengths emitted at a plurality of discrete spatial sample points from the agricultural sample;
- dispersing the emitted light of mixed wavelengths for each discrete spatial sample point into a corresponding spectral image comprising a plurality of component wavelengths;
- detecting, with respect to each discrete spatial sample point, component wavelengths within the corresponding spectral image; and
- processing the detected component wavelengths for each of the discrete spatial sample points on the agricultural sample against a model to identify one or more discrete spatial sample points as being associated with a certain portion of the agricultural sample, the model associating the existence of certain component wavelengths in the spectral image with certain portions of the agricultural sample.

121. The method of claim 120 wherein the emitted light comprises reflected light from the agricultural sample.

122. The method of claim 120 wherein the emitted light comprises transmitted light passed through the agricultural sample.

123. The method of claim 120 wherein the certain portion comprises an endosperm portion of the agricultural sample, and the step of processing further comprises the step of identifying the discrete spatial sample points associated with the endosperm portion.

124. The method of claim 123 wherein the step of processing further comprises the step of processing the detected component wavelengths for those identified discrete spatial sample points associated with the endosperm portion of the agricultural sample against a model to determine whether the agricultural product exhibits a certain trait in the endosperm portion, the model associating the existence of certain component wavelengths in the spectral image with the presence of the exhibited certain trait at the corresponding discrete spatial sample point for the agricultural product.

125. The method of claim 120 wherein the certain portion comprises a germ portion of the agricultural sample, and the step of processing further comprises the step of identifying the discrete spatial sample points associated with the germ portion.

126. The method of claim 125 wherein the step of processing further comprises the step of processing the detected component wavelengths for those identified discrete spatial sample points associated with the germ portion of the agricultural sample against a model to determine whether the agricultural product exhibits a certain trait in the germ portion, the model associating the existence of certain component wavelengths in the spectral image with the presence of the exhibited certain trait at the corresponding discrete spatial sample point for the agricultural product.

127. The method of claim 120 wherein the certain portion comprises an embryo portion of the agricultural sample, and the step of processing further comprises the step of identifying the discrete spatial sample points associated with the embryo portion.

128. The method of claim 127 wherein the step of processing further comprises the step of processing the detected component wavelengths for those identified discrete spatial sample points associated with the embryo portion of the agricultural sample against a model to determine whether the agricultural product exhibits a certain trait in the embryo portion, the model associating the existence of certain component wavelengths in the spectral image with the presence of the exhibited certain trait at the corresponding discrete spatial sample point for the agricultural product.

129. The method of claim 120 wherein the agricultural sample comprises a batch of seeds, and the certain portion comprises an individual seed in the batch of seeds, and the step of processing further comprises the step of identifying the discrete spatial sample points associated with the individual seeds.

130. The method of claim 129 wherein the step of processing further comprises the step of processing the detected component wavelengths for those identified discrete spatial sample points associated with an individual seed in the batch of seeds against a model to determine whether the agricultural product exhibits a certain trait in each of the individual seeds, the model associating the existence of certain component wavelengths in the spectral image with the presence of the exhibited certain trait at the corresponding discrete spatial sample point for the agricultural product.

131. The method of claim 120 further including step of sorting the agricultural sample among a plurality of destinations based on trait analysis of the certain portion.

132. The method of claim 120 further including the step of selecting the agricultural sample based on trait analysis of the certain portion.

133. Apparatus for differentially analyzing portions of an agricultural sample, comprising:
- a light source directing light on the agricultural sample to produce light of mixed wavelengths emitted at a plurality of discrete spatial sample points from the agricultural sample;
- a spectrograph that disperses the emitted light of mixed wavelengths for each discrete spatial sample point into a corresponding spectral image comprising a plurality of component wavelengths;
- a camera including a detector for detecting, with respect to each discrete spatial sample point, component wavelengths within the corresponding spectral image; and
- a processor operable to compare the detected component wavelengths for each of the discrete spatial sample points on the agricultural sample against a model to identify one or more discrete spatial sample points as being associated with a certain portion of the agricultural sample, the model associating the existence of certain component wavelengths in the spectral image with certain portions of the agricultural sample.

134. The apparatus of claim 133 wherein the emitted light comprises reflected light from the agricultural sample.

135. The apparatus of claim 133 wherein the emitted light comprises transmitted light passed through the agricultural sample.

136. The apparatus of claim 133 wherein the certain portion comprises an endosperm portion of the agricultural sample, and the processor further operates to identify the discrete spatial sample points associated with the endosperm portion.

137. The apparatus of claim 136 wherein the processor further operates to process the detected component wavelengths for those identified discrete spatial sample points associated with the endosperm portion of the agricultural sample against a model to determine whether the agricultural product exhibits a certain trait in the endosperm portion, the model associating the existence of certain component wavelengths in the spectral image with the presence of the exhibited certain trait at the corresponding discrete spatial sample point for the agricultural product.

138. The apparatus of claim 133 wherein the certain portion comprises a germ portion of the agricultural sample, and the processor further operates to identify the discrete spatial sample points associated with the germ portion.

139. The apparatus of claim 138 wherein the processor further operates to process the detected component wavelengths for those identified discrete spatial sample points associated with the germ portion of the agricultural sample against a model to determine whether the agricultural product exhibits a certain trait in the germ portion, the model associating the existence of certain component wavelengths in the spectral image with the presence of the exhibited certain trait at the corresponding discrete spatial sample point for the agricultural product.

140. The apparatus of claim 133 wherein the certain portion comprises an embryo portion of the agricultural sample, and the processor further operates to identify the discrete spatial sample points associated with the embryo portion.

141. The apparatus of claim 140 wherein the processor further operates to process the detected component wavelengths for those identified discrete spatial sample points associated with the embryo portion of the agricultural sample against a model to determine whether the agricultural product exhibits a certain trait in the embryo portion, the model associating the existence of certain component wavelengths in the spectral image with the presence of the exhibited certain trait at the corresponding discrete spatial sample point for the agricultural product.

142. The apparatus of claim 143 wherein the agricultural sample comprises a batch of seeds, and the certain portion comprises an individual seed in the batch of seeds, and the processor further operates to identify the discrete spatial sample points associated with the individual seeds.

143. The apparatus of claim 142 wherein the processor further operates to process the detected component wavelengths for those identified discrete spatial sample points associated with an individual seed in the batch of seeds against a model to determine whether the agricultural product exhibits a certain trait in each of the individual seeds, the model associating the existence of certain component wavelengths in the spectral image with the presence of the exhibited certain trait at the corresponding discrete spatial sample point for the agricultural product.

144. The apparatus of claim 143 further including a sorter that directs the seed among a plurality of destinations based on whether the seed is determined to be a haploid.

145. The apparatus of claim 143 further including a selector for choosing the seed based on a determination that the seed is a haploid.

146. A method, comprising the steps of:
- directing light on an agricultural sample to produce light of mixed wavelengths emitted at a plurality of discrete spatial sample points from the agricultural sample;
- dispersing the emitted light of mixed wavelengths for each discrete spatial sample points into a corresponding spectral image comprising a plurality of component wavelengths;
- detecting, with respect to each discrete spatial sample point, component wavelengths within the corresponding spectral image; and
- processing the detected component wavelengths to determine whether the agricultural sample exhibits a trait at individual ones of the discrete spatial sample points based on the component wavelengths within the corresponding spectral image.

147. The method according to claim 146, wherein said trait is one of a quantitative trait, a biochemical trait and a morphological trait.

148. The method according to claim 147, wherein said biochemical trait is selected from the group consisting of oil content, protein content, carbohydrate content, starch content, fiber content and water content.

149. The method according to claim 148 wherein the biochemical trait of starch further comprises a starch phenotype selected from the group consisting of amylopectin and amylose.

150. The method according to claim 147, wherein said biochemical trait is selected from the group consisting of oil composition, protein composition, carbohydrate composition, and fiber composition.

151. The method according to claim 147, wherein said agricultural sample is a seed or part of a seed and said morphological trait is selected from endosperm size, germ size, seed shape, seed size, seed color, seed surface texture, seed weight, seed density, and seed integrity.

152. The method according to claim 151, wherein said seed integrity is correlated to resistance or susceptibility to one of disease, insect infestation and fungal infestation.

153. The method according to claim 146, wherein the directed light and dispersed light have wavelengths in the range 900 to 1,700 nanometers.

154. The method according to claim 153, wherein said dispersed light provides a spectral dispersion of at least 150 nm/mm and at least a 20 nm spectral resolution.

155. The method according to claim 146, wherein the emitted light is selected from the group consisting of light reflected from the agricultural sample at each of the sample points and light transmitted through the agricultural sample at each of the sample points.

156. The method according to claim 146, wherein the step of processing includes the step of determining if more than one trait is exhibited.

157. The method according to claim 146, wherein said step of processing comprises the step of determining a relative spatial distribution of the trait within the agricultural sample.

158. The method according to claim 146, wherein the agricultural sample is selected from the group consisting of a single seed, a batch of seeds and a plant tissue.

159. The method according to claim 146 wherein the step of processing further comprises the step of determining a quantitative amount of the exhibited trait at each of the discrete spatial sample points.

160. The method according to claim 146 wherein the trait comprises endosperm mutation characteristics selected from the group consisting of reduced zeins in the endosperm and amino acid quantities.

161. The method according to claim 146 wherein the trait comprises an indicator of kernel breakage selected from the group consisting of the ratio of vitreous to non-vitreous endosperm, kernel density, average kernel weight, pericarp quantity, pericarp quality, kernel size and kernel shape.

162. The method according to claim 146 further including the step of:
measuring the weight of the agricultural sample; and
wherein the step of processing further includes the step of determining a quantitative amount of the exhibited trait per measured weight of the agricultural sample.

163. The method according to claim 146 further including step of sorting the agricultural sample among a plurality of destinations based on the determined presence of the exhibited certain trait.

164. The method according to claim 146 further including the step of selecting preferred individuals of the agricultural sample based on the determined presence of the exhibited certain trait.

165. The method according to claim 146,
wherein the step of directing light comprises the step of (A) directing a line of light on a portion of an agricultural sample to produce emitted light;
wherein the step of dispersing comprises the step of (B) dispersing the emitted light into the corresponding spectral image comprising the plurality of component wavelengths for each of the plurality of discrete spatial sample points on portion of the agricultural sample along the line of light;
wherein the step of detecting comprises the step of (C) detecting, with respect to each discrete spatial sample point along the line of light, component wavelengths within the corresponding spectral image;
further including the steps of:
repeating steps (A)–(C) to scan each portion of the agricultural sample; and
producing from the detected component wavelengths at each discrete spatial sample point for each of the scanned portions a hyperspectral datacube for the agricultural sample.

166. The method according to claim 165 wherein the step of processing includes the step of processing the detected component wavelengths in the hyperspectral datacube against a model to determine whether the agricultural sample exhibits a certain trait at each of the discrete spatial sample points, the model associating the existence of certain component wavelengths in the spectral image with the presence of the exhibited certain trait at the corresponding discrete spatial sample point for the agricultural sample.

167. The method according to claim 165 wherein the step of processing includes the step of processing the detected component wavelengths in the hyperspectral datacube associated with discrete spatial sample points in a certain portion against a model to determine whether the agricultural sample exhibits a certain trait at each of the discrete spatial sample points in that certain portion, the model associating the existence of certain component wavelengths in the spectral image with the presence of the exhibited certain trait at the corresponding discrete spatial sample points of the certain portion for the agricultural sample.

168. The method according to claim 165 wherein the step of processing includes the step of processing the detected component wavelengths in the hyperspectral datacube associated with discrete spatial sample points in a certain portion against a model to determine whether the agricultural sample exhibits a certain trait at the certain portion, the model associating the existence of certain component wavelengths in the spectral images for the discrete spatial sample points in the certain portion with the presence of the exhibited certain trait at the certain portion of the agricultural sample.

169. The method according to claim 168 further including the step of averaging the detected component wavelengths in the hyperspectral datacube associated with discrete spatial sample points in a certain portion to form an average spectrum for the certain portion for processing against the model.

170. The method according to claim 146, wherein the agricultural sample is a seed and the step of processing comprises the step of processing the detected component wavelengths for each of the discrete spatial sample points on the seed against a model to determine whether the seed is a haploid, the model associating the existence of certain component wavelengths in the spectral image with a phenotype produced by a haploid trait.

171. The method according to claim 170 wherein the step of processing further comprises the step of differentiating the location of the endosperm within the seed.

172. The method according to claim 171 wherein the step of processing further comprises the step of processing the detected component wavelengths for those discrete spatial sample points within the endosperm of the seed to detect anthocyainin coloration indicative of the seed being a haploid.

173. The method according to claim 170 wherein the step of processing further comprises the step of differentiating the location of the embryo within the seed.

174. The method according to claim 173 wherein the step of processing further comprises the step of processing the detected component wavelengths for those discrete spatial sample points within the embryo of the seed to detect a lack of coloration indicative of the seed being a haploid.

175. The method according to claim 146, wherein the step of processing further comprises the step of processing the detected component wavelengths against a model to determine whether the agricultural sample exhibits the trait at each of the discrete spatial sample points, the model associating the existence of certain component wavelengths in the spectral image with the presence of the exhibited trait at the corresponding discrete spatial sample point for the agricultural sample.

176. Apparatus, comprising:
a light source that directs light on an agricultural sample to produce light of mixed wavelengths emitted at a plurality of discrete spatial sample points from the agricultural sample;
a spectrograph that disperses the emitted light of mixed wavelengths for each discrete spatial sample points into a corresponding spectral image comprising a plurality of component wavelengths;
a light measuring device that detects, with respect to each discrete spatial sample point, component wavelengths within the corresponding spectral image; and
a processor operable to determine from detected component wavelengths whether the agricultural sample exhibits a trait at individual ones of the discrete spatial sample points based on the component wavelengths within the corresponding spectral image.

177. The apparatus according to claim 176, wherein said spectrograph is selected from the group consisting of a prism-grating-prism spectrograph or a reflective grating spectrograph.

178. The apparatus according to claim 176, wherein said light source is selected from the group consisting of halogen, tungsten halogen, long filament halogen, xenon, xenon flash, fluorescent, neon, and mercury.

179. The apparatus according to claim 176, wherein the light measuring device is selected from the group consisting of an Indium Antimonide camera, a Mercury Cadmium Telluride camera, a Platinum Silicide camera, an Arsenic-doped Silicon camera, an Indium Gallium Arsenide camera, and a CCD camera.

180. The apparatus according to claim 176, wherein said trait is one of a quantitative trait, a biochemical trait and a morphological trait.

181. The apparatus according to claim 180, wherein said biochemical trait is selected from the group consisting of oil content, protein content, carbohydrate content, starch content, fiber content and water content.

182. The apparatus according to claim 181 wherein the biochemical trait of starch further comprises a starch phenotype selected from the group consisting of amylopectin and amylose.

183. The apparatus according to claim 180, wherein said biochemical trait is selected from the group consisting of oil composition, protein composition, carbohydrate composition, and fiber composition.

184. The apparatus according to claim 180, wherein said agricultural sample is a seed or part of a seed and said morphological trait is selected from endosperm size, germ size, seed shape, seed size, seed color, seed surface texture, seed weight, seed density, and seed integrity.

185. The apparatus according to claim 184, wherein said seed integrity is correlated to resistance or susceptibility to one of disease, insect infestation and fungal infestation.

186. The apparatus according to claim 176, wherein the directed light and dispersed light have wavelengths in the range 900 to 1,700 nanometers.

187. The apparatus according to claim 186, wherein said dispersed light provides a spectral dispersion of at least 150 nm/mm and at least a 20 nm spectral resolution.

188. The apparatus according to claim 176, wherein the emitted light is selected from the group consisting of light reflected from the agricultural sample at each of the sample points and light transmitted through the agricultural sample at each of the sample points.

189. The apparatus according to claim 176, wherein the processing is further operable to determine if more than one trait is exhibited.

190. The apparatus according to claim 176, wherein the processor is further operable to determine a relative spatial distribution of the trait within the agricultural sample.

191. The apparatus according to claim 176, wherein the agricultural sample is selected from the group consisting of a single seed, a batch of seeds and a plant tissue.

192. The apparatus according to claim 176 wherein the processor is further operable to determine a quantitative amount of the exhibited trait at each of the discrete spatial sample points.

193. The apparatus according to claim 176 wherein the trait comprises endosperm mutation characteristics selected from the group consisting of reduced zeins in the endosperm and amino acid quantities.

194. The apparatus according to claim 176 wherein the trait comprises an indicator of kernel breakage selected from the group consisting of the ratio of vitreous to non-vitreous endosperm, kernel density, average kernel weight, pericarp quantity, pericarp quality, kernel size and kernel shape.

195. The apparatus according to claim 176 further including:
means for measuring the weight of the agricultural sample; and
wherein the processor is further operable to determine a quantitative amount of the exhibited trait per measured weight of the agricultural sample.

196. The apparatus according to claim 176 further including a sorting device that selects preferred individuals of the agricultural sample for delivery to certain destinations based on the determined presence of the exhibited certain trait.

197. The apparatus according to claim 176,
wherein the light source directs a line of light on a portion of an agricultural sample to produce emitted light;
wherein the spectrograph disperses the emitted light into the corresponding spectral image comprising the plurality of component wavelengths for each of the plurality of discrete spatial sample points on portion of the agricultural sample along the line of light;
wherein the light measuring device detects, with respect to each discrete spatial sample point along the line of light, component wavelengths within the corresponding spectral image;
further including:
means for moving the agricultural sample relative to the line of light to scan each portion of the agricultural sample.

198. The apparatus according to claim 197 wherein the processor is further operable to produce from the detected component wavelengths at each discrete spatial sample point for each of the scanned portions a hyperspectral datacube for the agricultural sample.

199. The apparatus according to claim 198 wherein the processor is further operable to process the detected component wavelengths in the hyperspectral datacube against a model to determine whether the agricultural sample exhibits a certain trait at each of the discrete spatial sample points, the model associating the existence of certain component wavelengths in the spectral image with the presence of the exhibited certain trait at the corresponding discrete spatial sample point for the agricultural sample.

200. The apparatus according to claim 198 wherein the processor is further operable to process the detected component wavelengths in the hyperspectral datacube associated with discrete spatial sample points in a certain portion against a model to determine whether the agricultural sample exhibits a certain trait at each of the discrete spatial sample points in that certain portion, the model associating the existence of certain component wavelengths in the spectral image with the presence of the exhibited certain trait at the corresponding discrete spatial sample points of the certain portion for the agricultural sample.

201. The apparatus according to claim 198 wherein the processor is further operable to process the detected component wavelengths in the hyperspectral datacube associated with discrete spatial sample points in a certain portion against a model to determine whether the agricultural sample exhibits a certain trait at the certain portion, the model associating the existence of certain component wavelengths in the spectral images for the discrete spatial sample points in the certain portion with the presence of the exhibited certain trait at the certain portion of the agricultural sample.

202. The apparatus according to claim 201 wherein the processor is still further operable to average the detected component wavelengths in the hyperspectral datacube associated with discrete spatial sample points in a certain portion to form an average spectrum for the certain portion for processing against the model.

203. The apparatus according to claim 197 further including:

a sample holder for holding the agricultural sample; and wherein the means for moving comprises a linear translation stage supporting the sample holder and operable to move the sample holder relative to the spectrograph to effectuate a scanning of light from the light source across, and the production of mixed wavelength lights emitted at a plurality of discrete spatial sample points over, the agricultural sample held therein.

204. The apparatus according to claim 176 further comprising a processing device selected from the group consisting of a sheller, thresher and combine for providing the agricultural sample.

205. The apparatus according to claim 176, wherein the agricultural sample is a seed and the processor is operable to process the detected component wavelengths for each of the discrete spatial sample points on the seed against a model to determine whether the seed is a haploid, the model associating the existence of certain component wavelengths in the spectral image with a phenotype produced by a haploid trait.

206. The apparatus according to claim 205 wherein the processor is further operable to differentiate the location of the endosperm within the seed and process the detected component wavelengths for those discrete spatial sample points within the endosperm of the seed to detect anthocyainin coloration indicative of the seed being a haploid.

207. The apparatus according to claim 205 wherein the processor is further operable to differentiate the location of the embryo within the seed and process the detected component wavelengths for those discrete spatial sample points within the embryo of the seed to detect a lack of coloration indicative of the seed being a haploid.

208. The apparatus according to claim 176, wherein the processor is further operable to process the detected component wavelengths against a model to determine whether the agricultural sample exhibits the trait at each of the discrete spatial sample points, the model associating the existence of certain component wavelengths in the spectral image with the presence of the exhibited trait at the corresponding discrete spatial sample point for the agricultural sample.

209. The apparatus according to claim 176, wherein said light measuring device is a camera possessing a focal plane having greater than 75,000 pixels, less than a 20 micron pitch, and a frame rate in excess of 25 frames per second.

* * * * *